United States Patent
Kaiser et al.

(10) Patent No.: US 12,084,476 B2
(45) Date of Patent: Sep. 10, 2024

(54) TAILORED CYCLODEPSIPEPTIDES AS POTENT NON-COVALENT SERINE PROTEASE INHIBITORS

(71) Applicant: UNIVERSITÄT DUISBURG-ESSEN, Essen (DE)

(72) Inventors: Markus Kaiser, Essen (DE); Steffen Köcher, Essen (DE); Juliana Rey, Essen (DE); Jens Bongard, Essen (DE); Michael Ehrmann, Essen (DE); Sarah Resch, Essen (DE)

(73) Assignee: UNIVERSITÄT DUISBURG-ESSEN, Essen (DE)

( * ) Notice: Subject to any disclaimer, the term of this patent is extended or adjusted under 35 U.S.C. 154(b) by 91 days.

(21) Appl. No.: 17/476,041

(22) Filed: Sep. 15, 2021

(65) Prior Publication Data

US 2022/0002348 A1 Jan. 6, 2022

Related U.S. Application Data

(62) Division of application No. 16/610,171, filed as application No. PCT/EP2018/062381 on May 14, 2018, now Pat. No. 11,149,067.

(30) Foreign Application Priority Data

May 12, 2017 (LU) .................................. LU100200

(51) Int. Cl.
| | |
|---|---|
| *C07K 11/02* | (2006.01) |
| *A61K 38/00* | (2006.01) |
| *C07K 1/10* | (2006.01) |
| *C12Q 1/37* | (2006.01) |

(52) U.S. Cl.
CPC ................ *C07K 11/02* (2013.01); *C07K 1/10* (2013.01); *C12Q 1/37* (2013.01); *A61K 38/00* (2013.01); *G01N 2500/04* (2013.01)

(58) Field of Classification Search
None
See application file for complete search history.

(56) References Cited

U.S. PATENT DOCUMENTS

| | | | |
|---|---|---|---|
| 11,149,067 B2 | 10/2021 | Kaiser et al. | |
| 2011/0124569 A1* | 5/2011 | Luesch ..................... | A61P 9/10 514/21.1 |
| 2020/0071360 A1 | 3/2020 | Kaiser et al. | |

FOREIGN PATENT DOCUMENTS

| | | |
|---|---|---|
| WO | 2008/101160 A2 | 8/2008 |
| WO | 2009/024528 A1 | 2/2009 |

OTHER PUBLICATIONS

Rubio et al. "Depsipeptides from a Guamanian marine cyanobacterium, Lyngbya bouillonii, with selective inhibition of serine proteases" Tetrahedron Letters 51:6718-6721. (Year: 2010).*
Plaza A and Bewley C "Largamides A-H, Unusual Cyclic Peptides from the Marine Cyanobacterium *Oscillatoria* sp." J. Organic Chemistry 71:6898-6907. (Year: 2006).*
Taori et al. "Lyngbyastatins 5-7, Potent Elastase Inhibitors from Floridian Marine Cyanobacteria *Lyngbya* spp." J. Natural Products 70:1593-1600. (Year: 2007).*
International Preliminary Report on Patentability, PCT/EP2018/062381, dated Nov. 12, 2019, 2018, 7 pages.
International Search Report and Written Opinion, PCT/EP2018/062381, dated Jul. 6, 2018, 10 pages.
Kocher S., et al., Tailored Ahp-cyclodepsipeptides as Potent Non-covalent Serine Protease Inhibitors, Angew Chem Int Ed, vol. 56(29): 8555-8558 (2017).
Plaza, A et al.,"Largamides A-H, Unusual Cyclic Peptides from the Marine Cyanobacterium *Oscillatoria* sp," The Journal of Organic Chemistry, vol. 71(18):6898-6907 (2006).
Rubio B K et al., "Depsipeptides from a Guamanian Marine Cyanobacterium, Lyngbya bouillonii, with Selective Inhibition of Serine Proteases," Tetrahedron Lett., vol. 51(51):6718-6721 (2010).
Stolze, S. et al., "Development of a Solid-Phase Approach to the Natural Product Class of Ahp-Containing Cyclodepsipeptides," European Journal of Organic Chemistry, vol. 2012 (8):1616-1625 (2012).
Stolze, S. et al., "Solid phase total synthesis of the 3-amino-6-hydroxy-2-piperidone (Ahp) cyclodepsipeptide and protease inhibitor Symplocamide A," Chemical Communications, vol. 46(46): 8857-8859 (2010).
Yokokawa et al. "Synthetic studies of micropeptin T-20, a novel 3-amino-6-hydroxy-2-piperidone (Ahp)-containing cyclic depsipeptide," Tetrahedron Lett., vol. 42:5903-5908. (2001).

* cited by examiner

*Primary Examiner* — Sudhakar Katakam
*Assistant Examiner* — Zachary J Miknis
(74) *Attorney, Agent, or Firm* — Nelson Mullins Riley & Scarborough LLP; Jane E. Remillard, Esq.; Jill Gorny Sloper, Esq.

(57) ABSTRACT

The present invention pertains to an improved chemical synthesis method for Ahp-cyclodepsipeptides which allows straight forward and easy synthesis of tailor-made Ahp-cyclodepsipeptides. The invention further provides Ahp-cyclodepsipeptides for use as HTRA protease inhibitors and their medical use.

9 Claims, 2 Drawing Sheets

TAILORED CYCLODEPSIPEPTIDES AS POTENT NON-COVALENT SERINE PROTEASE INHIBITORS

RELATED APPLICATIONS

This application is a divisional of U.S. application Ser. No. 16/610,171 (allowed), filed on Nov. 1, 2019, which is a 35 U.S.C. 371 national stage filing of International Application No. PCT/EP2018/062381, filed on May 14, 2018, which claims priority to Luxembourg Application No. LU100200, filed May 12, 2017, each of which are incorporated herein by reference in their entirety.

FIELD OF THE INVENTION

The present invention pertains to the field of protease inhibitors. An improved and versatile method for synthesizing cyclic peptides which function as inhibitors of serine proteases is provided. The structure and sequence of these cyclic peptides, especially Ahp-cyclodepsipeptides, can be adapted for specific binding and inhibition of a serine protease of interest. Furthermore, the present invention is directed to the use of Ahp-cyclodepsipeptides for inhibiting serine proteases, especially HTRA proteases. The present invention further provides certain cyclodepsipeptides which are potent inhibitors of HTRA proteases.

BACKGROUND OF THE INVENTION

Serine proteases of the S1 family (trypsin/chymotrypsin-like) are one of the largest and biomedically relevant protease families. In contrast to the design of covalent inhibitors or activity-based probes for this enzyme class, generic approaches for designing potent, enzyme class-specific, cellular active and non-covalent small molecule inhibitors are highly limited and have been achieved only for distinct serine proteases. Consequently, alternative approaches for the systematic generation of such chemical probes are urgently required.

One family of S1 serine proteases are HTRA proteases which are involved in certain diseases. In particular, severe diseases are based on deregulated HTRA1 hyperactivity such as age-related macular degeneration, polypoidal choroidal vasculopathy and arthritis while HTRA2 is involved for example in Parkinson's disease. However, no suitable inhibitors are yet available.

Figure 1:
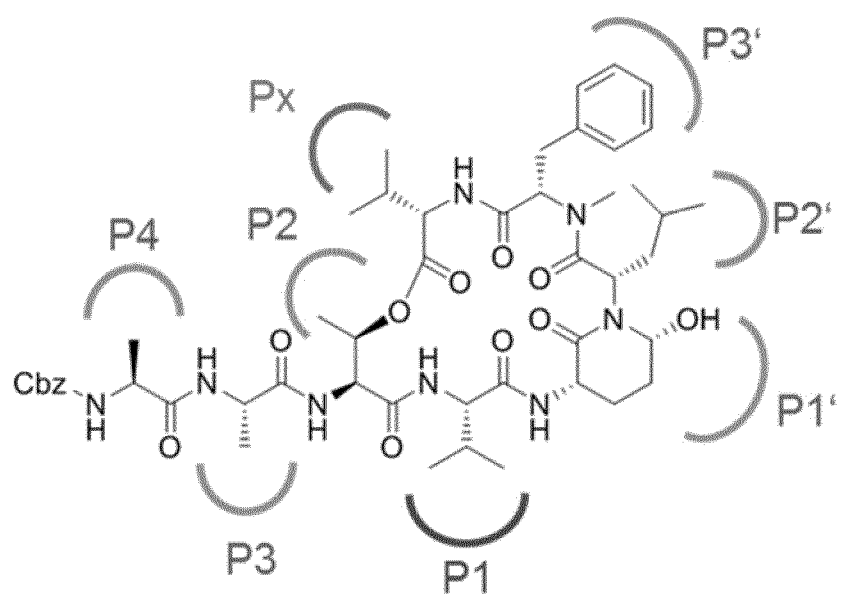

Ahp-cyclodepsipeptides (also termed cyanopeptolins or peptolides) are a class of over 100 peptidic natural products of non-ribosomal origin displaying potent serine protease inhibitory properties. All Ahp-cyclodepsipeptides are containing an Ahp (3-amino-6-hydroxy-2-piperidone) unit and an N-methyl aromatic amino acid at conserved positions in their 19-membered ring structure while other residues are much less conserved (FIG. 1). Structures of Ahp-cyclodepsipeptides:serine proteases complexes indicate that inhibition is based on a substrate-like binding mode in which distinct amino acid residues occupy S- and S'-pockets, however, proteolytic cleavage does not occur (FIG. 1b, Schechter and Berger nomenclature is used). Accordingly, they act similar to proteinaceous canonical serine protease inhibitors with the conserved residues stabilizing the inhibitory fold, while the other less conserved residues define serine protease selectivity via optimal accommodation to the specific S and S'-sites. Ahp-cyclodepsipeptides thus represent a suitable scaffold for tailoring non-covalent S1 serine protease inhibitors.

For generating such compounds, a practical synthesis for efficient generation of Ahp-cyclodepsipeptides was devised. So far, only few solution and one solid phase approach of Ahp-cyclodepsipeptides have been reported. Even the solid phase approach however requires a tedious and impractical multistep solution phase synthesis of a suitable Ahp-precursor building block.

It was therefore an object of the present invention to provide an alternative, straight-forward approach for synthesizing Ahp-cyclodepsipeptides. Furthermore, there was a need in the art for tailor-made inhibitors specific for distinct serine proteases, especially HTRA proteases.

SUMMARY OF THE INVENTION

The present inventors established a straight-forward combined solid and solution phase approach for synthesizing Ahp-cyclodepsipeptides. This synthesis route allows the rapid generation of Ahp-cyclodepsipeptide-based serine protease inhibitors. In particular, the developed effective combined solid and solution phase synthesis for Ahp-cyclodepsipeptides enabled the first synthesis of two natural products as well as the tailored design of HTRA protease inhibitors. The method was used to synthesize the currently most potent non-covalent HTRA1 and HTRA2 inhibitors, and activity in a cell based assay was demonstrated. Thereby new avenues for better characterizing of the cellular functions of these important protein quality control proteases by acute perturbation approaches are provided. Finally, the studies demonstrated the general suitability of Ahp-cyclodepsipeptides as a generic scaffold for the generation of non-covalent, bioactive serine protease inhibitors that not only bind to the protease S-sites but, in contrast to most classical serine protease inhibitory motifs, also accommodate S'-pockets. As the synthesis route allows also the facile incorporation of non-proteinogenic amino acids, this approach will facilitate the design of tailored, bioactive serine protease inhibitors and find wide application in future chemical probe design.

Therefore, in a first aspect, the present invention is directed to a method for synthesizing an Ahp-cyclodepsipeptide, comprising the steps of
(a) providing a resin loaded with 5-hydroxy-norvaline, named amino acid P1', wherein the 5-hydroxy-norvaline P1' is coupled to the resin via its 5-hydroxyl group forming an ether bond with the resin;
(b) adding 2 to 6 amino acids, named amino acid P1 to P6, to the 5-hydroxy-norvaline P1' using N terminal peptide synthesis, wherein the second amino acid P2 is an amino acid with a hydroxyl group in the side chain;
(c) adding an amino acid, named Px, to the hydroxyl group of the amino acid P2 via esterification with the α-carboxylic acid group of the amino acid;
(d) adding an N-methylated amino acid, named P3', to the amino acid Px added in step (c) using N terminal peptide synthesis;
(e) adding an amino acid, named P2', to the methylated amino group of the amino acid P3' added in step (d);
(f) forming a peptide pond between the α-carboxylic acid group of the 5-hydroxy-norvaline P1' and the α-amino group of the amino acid P2' added in step (e), thereby cyclizing the formed peptide;
(g) cleaving the cyclic peptide from the resin;
(h) oxidizing the peptide so that the 5-hydroxy-norvaline P1' and the amino acid P2' added in step (e) form a 3-amino-6-hydroxy-2-piperidone unit, thereby providing an Ahp-cyclodepsipeptide.

In a second aspect, the present invention provides an Ahp-cyclodepsipeptide having the following formula

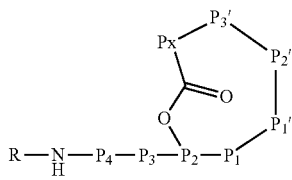

wherein
P1 is an amino acid with an aliphatic hydrophobic side chain;
P2 is an amino acid with a hydroxyl group in the side chain;
P3 is any amino acid or is absent;
P4 is any amino acid or is absent;
P1' is 5-hydroxy-norvaline forming a 3-amino-6-hydroxy-2-piperidone unit with the α-amino group of P2';
P2' is any amino acid;
P3' is an amino acid with a hydrophobic side chain comprising a methyl group attached to the α-amino group;
Px is any amino acid coupled with its α-carboxylic acid group to the hydroxyl group of P2, forming an ester bond;
R is hydrogen or a chemical group.

In a third aspect, the present invention is directed to the Ahp-cyclodepsipeptide according to the second aspect for use in the treatment of a HTRA-dependent disease. The present invention also provides a method for treating a patient afflicted with a HTRA-dependent disease, comprising the step of administering the patient in need thereof a therapeutically effective amount of an Ahp-cyclodepsipeptide as defined herein.

In a fourth aspect, the present invention provides a method for reducing or inhibiting the protease activity of a HTRA protease, comprising the step of contacting the HTRA protease with an Ahp-cyclodepsipeptide having the following formula

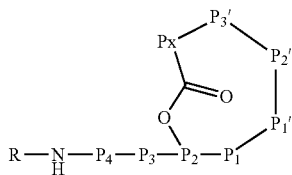

wherein
P1 is an amino acid with an aliphatic hydrophobic side chain;
P2 is an amino acid with a hydroxyl group in the side chain;
P3 is any amino acid or is absent;
P4 is any amino acid or is absent;
P1' is 5-hydroxy-norvaline forming a 3-amino-6-hydroxy-2-piperidone unit with the α-amino group of P2';
P2' is any amino acid;
P3' is an amino acid with a hydrophobic side chain comprising a methyl group attached to the α-amino group;
Px is any amino acid coupled with its α-carboxylic acid group to the hydroxyl group of P2, forming an ester bond;
R is hydrogen or a chemical group.

In a fifth aspect, the present invention provides a method of screening for an Ahp-cyclodepsipeptide capable of reducing or inhibiting the protease activity of a HTRA protease, comprising the steps of synthesizing an Ahp-cyclodepsipeptide using the method according to the first aspect, contacting an HTRA protease with the Ahp-cyclodepsipeptide, and determining the protease activity of the HTRA protease in the presence of the Ahp-cyclodepsipeptide.

Other objects, features, advantages and aspects of the present invention will become apparent to those skilled in the art from the following description and appended claims. It should be understood, however, that the following description, appended claims, and specific examples, which indicate preferred embodiments of the application, are given by way of illustration only. Various changes and modifications within the spirit and scope of the disclosed invention will become readily apparent to those skilled in the art from reading the following.

Definitions

As used herein, the following expressions are generally intended to preferably have the meanings as set forth below, except to the extent that the context in which they are used indicates otherwise.

The expression "comprise", as used herein, besides its literal meaning also includes and specifically refers to the expressions "consist essentially of" and "consist of". Thus, the expression "comprise" refers to embodiments wherein the subject-matter which "comprises" specifically listed elements does not comprise further elements as well as embodiments wherein the subject-matter which "comprises" specifically listed elements may and/or indeed does encompass further elements. Likewise, the expression "have" is to be understood as the expression "comprise", also including and specifically referring to the expressions "consist essentially of" and "consist of". The term "consist essentially of", where possible, in particular refers to embodiments wherein the subject-matter comprises 20% or less, in particular 15% or less, 10% or less or especially 5% or less further elements in addition to the specifically listed elements of which the subject-matter consists essentially of.

A "HTRA protease" as used herein refers to human HTRA1, human HTRA2, human HTRA3 and human HTRA4 and any isoforms or variants thereof as well as any homologues thereof in other species. In certain embodiments, the HTRA protease specifically refers to HTRA1. The protease activity of HTRA proteases in particular refers to the activity of the HTRA proteases to proteolytically cleave proteins, in particular specific proteins such as tau proteins, tubulins, beta-casein and extracellular matrix proteins The term "HTRA1" as used herein in particular refers to the serine protease HTRA1, including the precursor protein containing the N terminal signal peptide and the processed mature protein without the signal peptide. The HTRA1 may be from any species, but in particular is human HTRA1. The term "protease activity of HTRA1" as used herein in particular refers to the activity to proteolytically cleave tau proteins, tubulins or extracellular matrix proteins such as fibronectin.

The term "HTRA2" as used herein in particular refers to the serine protease HTRA2, including the precursor protein containing the N terminal signal peptide and the processed mature protein without the signal peptide. The HTRA2 may be from any species, but in particular is human HTRA2.

The term "HTRA3" as used herein in particular refers to the serine protease HTRA3, including the precursor protein containing the N terminal signal peptide and the processed mature protein without the signal peptide. The HTRA3 may be from any species, but in particular is human HTRA3. The term "protease activity of HTRA3" as used herein in particular refers to the activity to proteolytically cleave beta-casein or extracellular matrix proteins such as fibronectin.

The term "HTRA4" as used herein in particular refers to the serine protease HTRA4, including the precursor protein containing the N terminal signal peptide and the processed mature protein without the signal peptide. The HTRA4 may be from any species, but in particular is human HTRA4.

The term "Ahp-cyclodepsipeptide" as used herein refers to an amino acid peptide which comprises a 3-amino-6-hydroxy-2-piperidone ("Ahp") unit and forms a circular peptide. The Ahp-cyclodepsipeptide may comprise natural and/or non-natural amino acids. Cyclization of the Ahp-cyclodepsipeptide generally is achieved by coupling of the N terminus or C terminus, in particular the C terminus, with a side chain of one of the amino acids of the peptide.

"Amino acid" as referred to herein generally refers to any natural or non-natural amino acid, especially to α-amino acids wherein the carboxylic acid group and the amino group both are attached to the first carbon atom. The term "amino acid" generally refers to amino acids in L-conformation at the α carbon atom, i.e. the L-stereoisomers of the amino acids. The terms "α-amino group" and "α-carboxylic acid group" refer to the amino and carboxylic acid group present at the α-carbon atom, which form the peptide bonds in peptide synthesis. Natural amino acids include all amino acids which are found in and/or produced by living organisms. Natural amino acids in particular are alanine (ala—A), arginine (arg—R), asparagine (asn—N), aspartic acid (asp—D), cysteine (cys—C), glutamine (gln—Q), glutamic acid (glu—E), glycine (gly—G), histidine (his—H), isoleucine (ile—I), leucine (leu—L), lysine (lys—K), methionine (met—M), phenylalanine (phe—F), proline (pro—P), serine (ser—S), threonine (thr—T), tryptophan (trp—W), tyrosine (tyr—Y) and valine (vat—V). Non-natural amino acids are amino acids, i.e. molecules comprising a carboxylic acid group and an amino group, especially both attached to the α-carbon atom, which are not natural amino acids. An exemplary non-natural amino acid is 5-hydroxy-norvaline. 5-Hydroxy-norvaline is an α-amino acid with a 3-hydroxy-propyl group as side chain. Further examples are norvaline, an α-amino acid with a n-propyl group as side chain, homoalanine, an α-amino acid with an ethyl group as side chain, and homophenylalanine, an α-amino acid with an 2-phenylethyl group as side chain.

Amino acids with a hydrophobic side chain refer to any amino acids having a side chain which is mainly hydrophobic. Amino acids with a hydrophobic side chain in particular have an alkyl, especially a C1-8 alkyl, such as a C1-4 alkyl, as side chain. Examples of hydrophobic amino acids include Ala, Val, Ile, Leu, Met, Phe, Tyr and Trp. Amino acids with an aliphatic hydrophobic side chain include Ala, Val, Ile, Leu and Met. Amino acids with a C1-3 aliphatic hydrophobic side chain include Ala and Val. Amino acids with an aromatic hydrophobic side chain include Phe, Tyr and Trp. Other examples of amino acids with a hydrophobic side chain, in particular an alkyl, especially a C1-8 alkyl, such as a C1-4 alkyl, as side chain, include non-natural amino acids such as homoalanine, norvaline, an α-amino acid with a cyclopropyl group as side chain, and an α-amino acid with a 1,1-dimethylethyl group as side chain.

Amino acids with a hydroxyl group in the side chain may comprise any side chain as long as it comprises a hydroxyl group. Suitable examples include Ser and Thr, but also other amino acids wherein a hydroxyl group is added to the side chain of a natural amino acid, such as (3-OH)-phenylalanine or (3-OH)-leucine, wherein a hydroxyl group is added to the β carbon atom (the first carbon atom of the side chain) of phenylalanine or leucine, respectively. Amino acids with a hydroxyl group in the aliphatic side chain include, for example, Ser, Thr and (3-OH)-Leu.

Amino acids with a polar side chain refer to any amino acids having a side chain which is mainly hydrophilic, including amino acids with electrically charged side chain and amino acids with uncharged polar side chain. Suitable examples of amino acids with uncharged polar side chain include Ser, Thr, Asn and Gln, but also non-natural amino acids with a hydroxyl group, amide group, a halogen or a nitrile group in the side chain. Suitable examples of amino acids with charged side chain include Asp, Glu, Arg, His and Lys, but also non-natural amino acids with charged group such as a carboxylic acid group, amine group, a halogen or a nitrile group in the side chain.

Amino acids with an aromatic group in the side chain may comprise any side chain as long as it comprises an aromatic group. Suitable examples include phenylalanine, tyrosine, tryptophan and histidine, but also derivatives thereof such as homophenylalanine and phenylalanine wherein a further group is attached to the aromatic ring, for example p-chlorophenylalanine, m-chlorophenylalanine, p-bromophenylalanine, m-fluorophenylalanine and m-cyanophenylalanine.

A "chemical group" can be any organic or inorganic chemical moiety and includes optionally substituted aliphatic and aromatic groups, in particular optionally substituted C1-C20 alkyl, optionally substituted C1-C20 heteroalkyl, optionally substituted C6-C20 aryl and optionally substituted C6-C20 heteroaryl.

The term "patient" means according to the invention a human being, a nonhuman primate or another animal, in particular a mammal such as a cow, horse, pig, sheep, goat, dog, cat or a rodent such as a mouse and rat. In a particularly preferred embodiment, the patient is a human being.

The term "pharmaceutical composition" particularly refers to a composition suitable for administering to a human or animal, i.e., a composition containing components which are pharmaceutically acceptable. Preferably, a pharmaceutical composition comprises an active compound or a salt or prodrug thereof together with a carrier, diluent or pharmaceutical excipient such as buffer, preservative and tonicity modifier.

Numeric ranges described herein are inclusive of the numbers defining the range. The headings provided herein are not limitations of the various aspects or embodiments of this invention which can be read by reference to the specification as a whole. According to one embodiment, subject-matter described herein as comprising certain steps in the case of methods or as comprising certain ingredients in the case of compositions refers to subject-matter consisting of the respective steps or ingredients.

It is preferred to select and combine preferred aspects and embodiments described herein and the specific subject-matter arising from a respective combination of preferred embodiments also belongs to the present disclosure.

DETAILED DESCRIPTION OF THE INVENTION

The present invention is based on the development of a novel, straight forward and versatile method for synthesizing Ahp-cyclodepsipeptides. Furthermore, the inventors found that these Ahp-cyclodepsipeptides can be tailor-made to specifically and strongly bind to HTRA proteases, thereby inhibiting their protease activity. Inhibition of different HTRA proteases by various Ahp-cyclodepsipeptides was demonstrated.

The Synthesis Method

In view of these findings, the present invention provides in a first aspect a method for synthesizing an Ahp-cyclodepsipeptide, comprising the steps of
(a) providing a resin loaded with 5-hydroxy-norvaline, named amino acid P1', wherein the 5-hydroxy-norvaline P1' is coupled to the resin via its 5-hydroxyl group forming an ether bond with the resin;
(b) adding 2 to 6 amino acids, named amino acid P1 to P6, to the 5-hydroxy-norvaline P1' using N terminal peptide synthesis, wherein the second amino acid P2 is an amino acid with a hydroxyl group in the side chain;
(c) adding an amino acid, named Px, to the hydroxyl group of the amino acid P2 via esterification with the α-carboxylic acid group of the amino acid;
(d) adding an N-methylated amino acid, named P3', to the amino acid Px added in step (c) using N terminal peptide synthesis;
(e) adding an amino acid, named P2', to the methylated amino group of the amino acid P3' added in step (d);
(f) forming a peptide pond between the α-carboxylic acid group of the 5-hydroxy-norvaline P1' and the α-amino group of the amino acid P2' added in step (e), thereby cyclizing the formed peptide;
(g) cleaving the cyclic peptide from the resin;
(h) oxidizing the peptide so that the 5-hydroxy-norvaline P1' and the amino acid P2' added in step (e) form a 3-amino-6-hydroxy-2-piperidone unit, thereby providing an Ahp-cyclodepsipeptide.

The Ahp-cyclodepsipeptide is a peptide comprising 6 to 10 amino acids (depending on the presence or absence of P3, P4, P5 and/or P6) with the following sequence from N terminus to C terminus: (P6)-(P5)-(P4)-(P3) P2-P1-P1'-P2'-P3'-Px, wherein the carboxylic acid group of Px is coupled via an ester bond to the side chain hydroxyl group of P2. Furthermore, P1' forms a 3-amino-6-hydroxy-2-piperidone unit together with the α-amino group of P2', and a methyl group is attached to the α-amino group of P3'. A chemical group R may be coupled to the N terminus. In particular, the Ahp-cyclodepsipeptide may have the following formula:

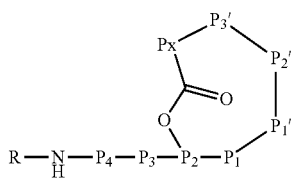

In this formula, P3 and P4 are shown while P5 and P6 are not shown. However, P3 and P4 are only optional and either P3 or P4 or both P3 and P4 may be absent. Furthermore, P5 and/or P6, if present, are represented by the unit "R" in the formula. The "—NH—" group in the formula is part of the N terminal amino acid P4 (or P3, if P4 is absent, or P2, if P3 and P4 are absent) and is only shown to indicate the N terminus of the peptide. Likewise, the "—O—C(=O)—" group between P2 and Px indicates the ester bond formed by the hydroxyl group of the side chain of P2 and the α-carboxylic acid group of Px. Hence, also these atoms are part of the amino acids P2 and Px. Without indicating the N terminus and the ester bond, the Ahp-cyclodepsipeptide may have the following formula:

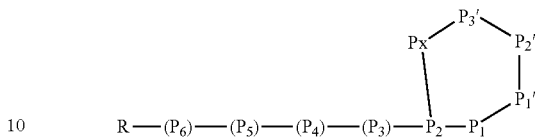

One of the key features of the method for synthesizing an Ahp-cyclodepsipeptide is the use of a resin to which the 5-hydroxy-norvaline is coupled via its 5-hydroxyl group forming an ether bond with the resin. This allows easy cleavage of the peptide from the resin as an alcohol comprising the 5-hydroxyl group of 5-hydroxy-norvaline. Thereby, straightforward reactions can be used for cleavage in step (g) and oxidation in step (h).

In certain embodiments, the resin is a chlorotrityl resin, especially a 2-chlorotrityl resin. Other suitable resins include trityl resin, Wang resin or the Merrifield resin.

For the different synthesis steps, amino acids may be used which comprise protecting groups. These protecting groups are in particular attached to the functional groups of the amino acids, such as the α-amino group or the α-carboxylic acid group or any functional groups in the side chain, depending on the specific synthesis chemistry used. For example, in certain embodiments the 5-hydroxy-norvaline P1' on the resin provided in step (a) is protected at the amino group and the carboxylic acid group, in particular with fluorenylmethyloxycarbonyl (Fmoc) at the amino group and allylester at the carboxylic acid group.

In certain embodiments, the N terminal peptide synthesis used in step (b) and/or (d) is performed via Fmoc/tBu strategy. In these embodiments, the α-amino group of a new amino acid is protected by Fmoc and sensible side chain functional groups are protected by tertiary butyl (tBu). Each cycle of adding a new amino acid is performed using the steps of deprotecting the amino acid at the N terminus, washing, attaching the new amino acid protected at the N terminus, and again washing. Other methods suitable for N terminal peptide synthesis are well known in the art and can readily be used by the skilled person.

In step (b), at least 2 amino acids, named amino acid P1 and P2, are added to P1'. Addition of P3, P4, P5 and/or P6 is optional. In certain embodiments, 2, 3 or 4 amino acids, named amino acid P1, P2, P3 and P4, are added.

In specific embodiments, esterification in step (c) is performed with a coupling agent such as diisopropylcarbodiimide (DIC) or dicyclohexylcarbodiimide (DCC), in particular DIC, and a catalyst such as 4-N,N-dimethylaminopyridine (DMAP). A suitable solvent such as dichloromethane (DCM) may be used and the reaction may progress at 25° C. or more, such as about 40° C., for at least 15 min, such as about 60 min. The esterification reaction in step (c) may be repeated at least once, such as one, two three, four or five timed, in particular four times. After each esterification reaction, the resin may be washed, for example with DCM or dimethyl formamide (DMF).

In certain embodiments, in step (e) the addition reaction of the amino acid P2' to the methylated amino group of the amino acid P3' is performed via phosphonium-mediated coupling. In particular, a phosphonium salt such as bromo-tri-pyrrolidino-phosphonium hexafluorophosphate (PyBroP) and/or a base such as diisopropylethylamine (DIPEA)

are used. A suitable solvent such as DCM may be used and the reaction may progress at 25° C. or more, such as about 40° C., for at least 15 min, such as about 60 min. The coupling reaction in step (e) may be repeated at least once, such as one, two three, four or five timed, in particular five times. After each coupling reaction, the resin may be washed, for example with DCM or DMF.

In embodiments wherein in step (a) the carboxylic acid group of the 5-hydroxy-norvaline P1' is protected, said protection is removed before the peptide bond is formed in step (f). For example, if an allyl protecting group is used, deprotection may be performed using tetrakis(triphenylphosphine)palladium(0) and morpholine. In certain embodiments, the peptide bond is formed in step (f) using a coupling reagent such as 2-(1H-benzotriazol-1-yl)-1,1,3,3-tetramethyluronium hexafluorophosphate (HBTU). Other known coupling reagents for forming a peptide bond may also be used. Additionally, a base such as DIPEA and a compound for forming activated esters such as hydroxybenzotriazole (HOBt) may be used. A suitable solvent such as DMF may be used and the reaction may progress for at least 1 hour, such as overnight. After the coupling reaction, the resin may be washed, for example with DCM, N-methylpyrrolidone (NMP) and/or DMF.

In step (g), the peptide may be cleaved from the resin using an acid such as trifluoroacetic acid (TFA), especially in a solution comprising TFA, triisopropylsilane and water, for example for at least 30 min, such as about 2 hours. In certain embodiments, the peptide is cleaved from the resin in step (g) using a strong acid, especially a strong acid in an aqueous solution. Suitable strong acids have a $pK_a$ value of 4 or below, in particular of 1 or below. The skilled person is capable of selecting a suitable acid. After the cleavage reaction, the obtained peptide may be purified, for example by evaporation of the solvent and the TFA to dryness.

In certain embodiments, the oxidation reaction in step (h) is performed via various oxidation reagents, in particular using Dess-Martin periodinane. The skilled person is capable of selecting a suitable oxidation reagent. Oxidation may be performed in an organic solvent. A suitable solvent such as DCM may be used and the reaction may progress for at least 15 min, such as about 60 min. Then the solution may be evaporated and the residue dissolved in a suitable solvent such as acetonitrile and water and stirred, e.g. overnight. In particular embodiments, the peptide is purified between steps (g) and (h) and/or after step (h).

Using the method for synthesizing an Ahp-cyclodepsipeptide as described herein, any amino acids, including natural and non-natural amino acids, can be introduced in the Ahp-cyclodepsipeptide. In particular, the amino acids at positions P1 to P6, P1', P2' and Px can be chosen at will, as long as the side chain of amino acid P2 comprises a hydroxyl group. In particular, the side chains of the amino acids added in steps (b), (c), (d) and (e) can be selected for binding to a target serine protease. In certain embodiments, the N-methylated amino acid P3' added in step (d) is an aromatic amino acid, in particular phenylalanine or tyrosine. In further embodiments, the amino acid P2 comprising a hydroxyl group in its side chain is selected from threonine, (3-OH)-phenylalanine and (3-OH)-leucine. In particular, the amino acids are selected in the method for synthesizing an Ahp-cyclodepsipeptide so that any of the Ahp-cyclodepsipeptides described herein are produced. In certain embodiments, at least one, especially at least two, of the amino acids P3, P4, P5, P6, P2' and Px have a polar side chain. Especially, the one or two amino acids having a polar side chain are P3, P4, P2' and/or Px. Suitable amino acids having a polar side chain include, for example, Asn and Gln.

In certain embodiments, the last amino acid added in step (b), i.e. P2, P3, P4, P5 or P6 depending on the presence of P3, P4, P5 and/or P6, may comprise a chemical group attached to its α-amino group. The chemical group may already be present in the amino acid building block attached to the growing peptide chain or the method for synthesizing an Ahp-cyclodepsipeptide may comprise the further step of coupling a chemical group to the N terminus of the peptide. The chemical group may be any group suitable for attaching to the N terminus of a peptide. In particular, the chemical group may be a C1-15 aliphatic or aromatic alkyl group forming an amide bond or a carbamate bond with the amino group to which it is attached.

The Ahp-Cyclodepsipeptides

In a further aspect, the present invention provides an Ahp-cyclodepsipeptide having the following formula

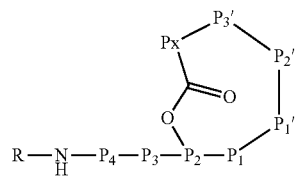

wherein
P1 is an amino acid with an aliphatic hydrophobic side chain;
P2 is an amino acid with a hydroxyl group in the side chain;
P3 is any amino acid or is absent;
P4 is any amino acid or is absent;
P1' is 5-hydroxy-norvaline forming a 3-amino-6-hydroxy-2-piperidone unit with the α-amino group of P2';
P2' is any amino acid;
P3' is an amino acid with a hydrophobic side chain comprising a methyl group attached to the α-amino group;
Px is any amino acid coupled with its α-carboxylic acid group to the hydroxyl group of P2, forming an ester bond; and
R is hydrogen or a chemical group.

Without indicating the amino group of the N terminus and the ester bond between R2 and Rx, the formula of the Ahp-cyclodepsipeptide may be written as follows:

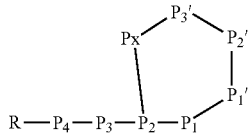

In specific embodiments,
P1 is an amino acid with an aliphatic hydrophobic side chain;
P2 is an amino acid with a hydroxyl group in the side chain;
P3 is an amino acid with a hydrophobic or aromatic side chain or is absent;
P4 is an amino acid with an aliphatic hydrophobic side chain or is absent;

P1' is 5-hydroxy-norvaline forming a 3-amino-6-hydroxy-2-piperidone unit with the α-amino group of P2';
P2' is an amino acid with a hydrophobic, aromatic or hydrophilic side chain;
P3' is an amino acid with a hydrophobic side chain comprising a methyl group attached to the α-amino group;
Px is an amino acid with a hydrophobic side chain coupled with its α-carboxylic acid group to the hydroxyl group of P2, forming an ester bond; and
R is hydrogen or a chemical group.

P1, P2, P3, P4, P2', P3' and Px each may be a natural or a non-natural amino acid. All these amino acids may be selected independently of each other.

In certain embodiments, P1 is an amino acid with a C1-3 aliphatic hydrophobic side chain. P1 may be selected from the group consisting of alanine, valine, leucine, isoleucine homoalanine, norvaline, an α-amino acid with a cyclopropyl group as side chain, and an α-amino acid with a 1,1-dimethylethyl group as side chain, especially valine, leucine and an α-amino acid with a cyclopropyl group as side chain. In particular, P1 is valine. In specifically preferred embodiments, P1 is an α-amino acid with a cyclopropyl group as side chain.

In certain embodiments, P2 is an amino acid with an aliphatic side chain comprising a hydroxyl group. P2 may be selected from the group consisting of threonine, (3-OH)-phenylalanine, (3-OH)-leucine, tyrosine and serine, especially threonine, (3-OH)-phenylalanine and (3-OH)-leucine. In particular, P2 is threonine or (3-OH)-leucine. In specific embodiments, P2 is not threonine.

In certain embodiments, P3 is an amino acid with a hydrophobic side chain, especially with an aliphatic hydrophobic side chain, in particular with a C1-3 aliphatic hydrophobic side chain. P3 may be selected from the group consisting of alanine, valine, leucine, isoleucine, phenylalanine, tyrosine and tryptophan, especially alanine, valine and phenylalanine. In particular, P3 is alanine. In further embodiments, P3 is an amino acid with an aromatic side chain. P3 may be selected from the group consisting of phenylalanine, tyrosine, phenylalanine wherein the phenyl ring is substituted with a halogen or a nitrile group, and homophenylalanine, especially phenylalanine, p-chlorophenylalanine, m-chlorophenylalanine, m-fluorophenylalanine and m-cyanophenylalanine. In particular, P3 is m-fluorophenylalanine.

In certain embodiments, P4 is an amino acid with a hydrophobic side chain, especially with an aliphatic hydrophobic side chain, in particular with a C1-3 aliphatic hydrophobic side chain. P4 may be selected from the group consisting of alanine, valine, leucine and isoleucine, especially alanine and valine. In particular, P4 is alanine. Alternatively, P4 is absent.

In certain embodiments, P2' is an amino acid with a hydrophobic side chain, especially with an aliphatic hydrophobic side chain. P2' may be selected from the group consisting of alanine, valine, leucine, isoleucine, phenylalanine, tyrosine and tryptophan, especially leucine, isoleucine and phenylalanine. In particular, P2' is leucine. In further embodiments, P2' is an amino acid with a hydrophilic side chain. P2' may be selected from the group consisting of glutamic acid, aspartic acid, glutamine, asparagine, arginine, phenylalanine, phenylalanine wherein the phenyl ring is substituted with a halogen or a nitrile group, and homophenylalanine especially glutamic acid, asparagine, phenylalanine, p-chlorophenylalanine, p-bromophenylalanine, m-fluorophenylalanine, m-cyanophenylalanine and an α-amino acid with a —$CH_2CH_2CH_2NHC(=O)NH_2$ group as side chain. In particular, P2' is p-chlorophenylalanine or phenylalanine.

In certain embodiments, P3' is an amino acid with an aromatic hydrophobic side chain comprising a methyl group attached to the α-amino group. P3' may be selected from the group consisting of alanine, valine, leucine, isoleucine, phenylalanine, tyrosine and tryptophan, especially phenylalanine, tyrosine and alanine. In particular, P3' is phenylalanine.

In certain embodiments, Px is an amino acid with a hydrophobic side chain, especially with an aliphatic hydrophobic side chain, in particular with a C1-3 aliphatic hydrophobic side chain. Px may be selected from the group consisting of alanine, valine, leucine, isoleucine, phenylalanine, tyrosine and tryptophan, especially alanine, valine and phenylalanine. In particular, Px is valine.

In specific embodiments, at least one, especially at least two, of the amino acids P3, P4, P2' and Px have a polar side chain. Suitable amino acids having a polar side chain include, for example, Asn and Gln.

In certain embodiments, R is hydrogen or a C1-15, especially C1-8, aliphatic or aromatic alkyl group forming an amide bond or a carbamate bond with the amino group to which it is attached. In certain embodiments, R is hydrogen. In other embodiments, R is a protecting group such as carboxybenzyl. In further embodiments, R is an acyl group, especially a C1-8 acyl group such as acetyl, propionyl, butyryl and benzoyl. In further embodiments, R includes or consists of one or more amino acids, especially one or two amino acids, named R5 and R6, attached via peptide bonds to R4. These further amino acids may be any amino acids, and in particular R5 and/or R6 may be amino acids with a polar side chain. In these embodiments, R may further include a C1-15 aliphatic or aromatic alkyl group or a protecting group attached to the N terminus of these further amino acids.

The Ahp-cyclodepsipeptide may be obtainable or obtained by the method for synthesizing an Ahp-cyclodepsipeptide as described herein.

The Ahp-cyclodepsipeptide in particular is capable of binding to one or more HTRA proteases and reducing or inhibiting its protease activity. In certain embodiments, the HTRA protease is selected from the group consisting of human HTRA1, human HTRA2 and human HTRA3, especially human HTRA1 or human HTRA2, preferably human HTRA1.

The Ahp-cyclodepsipeptide capable of binding to human HTRA1 and reducing or inhibiting its protease activity in particular has the following features:
P1 is an amino acid with a C1-3 aliphatic hydrophobic side chain;
P2 is an amino acid with a hydroxyl group in the aliphatic side chain;
P3 is an amino acid with an aliphatic hydrophobic side chain;
P4 is an amino acid with an aliphatic hydrophobic side chain;
P1 ' is 5-hydroxy-norvaline forming a 3-amino-6-hydroxy-2-piperidone unit with the α-amino group of P2';
P2' is an amino acid with a hydrophobic side chain;
P3' is an amino acid with an aromatic hydrophobic side chain comprising a methyl group attached to the α-amino group;

Px is an amino acid with an aliphatic hydrophobic side chain coupled with its α-carboxylic acid group to the hydroxyl group of P2, forming an ester bond;

R is hydrogen or a C1-15 aliphatic or aromatic alkyl group forming an amid bond or a carbamate bond with the amino group to which it is attached.

In certain embodiments, in the Ahp-cyclodepsipeptide capable of binding to human HTRA1 and reducing or inhibiting its protease activity P1 is alanine, valine, homoalanine, norvaline or an α-amino acid with a cyclopropyl group as side chain, in particular valine;

P2 is threonine or (3-OH)-leucine, in particular (3-OH)-leucine;

P3 is alanine or valine, in particular alanine;

P4 is alanine or valine, in particular alanine;

P1' is 5-hydroxy-norvaline forming a 3-amino-6-hydroxy-2-piperidone unit with the α-amino group of P2';

P2' is leucine, isoleucine or phenylalanine, in particular leucine or phenylalanine;

P3' is phenylalanine or tyrosine, in particular phenylalanine, comprising a methyl group attached to the α-amino group;

Px is alanine or valine, in particular valine, coupled with its α-carboxylic acid group to the hydroxyl group of P2, forming an ester bond;

R is hydrogen or a C1-8 aliphatic or aromatic alkyl group forming an amid bond or a carbamate bond with the amino group to which it is attached.

Especially, in the Ahp-cyclodepsipeptide capable of binding to human HTRA1 and reducing or inhibiting its protease activity P1 is valine, alanine, homoalanine, norvaline or an α-amino acid with a cyclopropyl group as side chain;

P2 is threonine or (3-OH)-leucine, in particular (3-OH)-leucine;

P3 is alanine;

P4 is alanine;

P1' is 5-hydroxy-norvaline forming a 3-amino-6-hydroxy-2-piperidone unit with the α-amino group of P2';

P2' is leucine or phenylalanine, in particular leucine;

P3' is phenylalanine comprising a methyl group attached to the α-amino group;

Px is valine coupled with its α-carboxylic acid group to the hydroxyl group of P2, forming an ester bond;

R is hydrogen or a C1-8 aliphatic or aromatic alkyl group forming an amid bond or a carbamate bond with the amino group to which it is attached.

In specific embodiments of the above Ahp-cyclodepsipeptide capable of binding to human HTRA1 and reducing or inhibiting its protease activity, P1 is valine, alanine, homoalanine, norvaline or an α-amino acid with a cyclopropyl group as side chain, P2 is threonine and P2' is leucine. In further embodiments of the above Ahp-cyclodepsipeptide capable of binding to human HTRA1 and reducing or inhibiting its protease activity, P1 is valine, P2 is threonine or (3-OH)-leucine and P2' is leucine. In further embodiments of the above Ahp-cyclodepsipeptide capable of binding to human HTRA1 and reducing or inhibiting its protease activity, P1 is valine, P2 is threonine and P2' is phenylalanine.

The Ahp-cyclodepsipeptide capable of binding to human HTRA2 and reducing or inhibiting its protease activity in particular has the following features:

P1 is alanine, valine, leucine, isoleucine, homoalanine, norvaline or an α-amino acid with a cyclopropyl group as side chain, in particular valine or leucine;

P2 is threonine, (3-OH)-phenylalanine or (3-OH)-leucine, in particular (3-OH)-phenylalanine or (3-OH)-leucine;

P3 is alanine, valine, leucine, isoleucine, phenylalanine or tyrosine, in particular alanine, phenylalanine or tyrosine, especially phenylalanine;

P4 is alanine or valine, in particular alanine, or is absent;

P1' is 5-hydroxy-norvaline forming a 3-amino-6-hydroxy-2-piperidone unit with the α-amino group of P2';

P2' is leucine, isoleucine or phenylalanine, in particular leucine or phenylalanine;

P3' is alanine, valine, leucine, isoleucine, phenylalanine or tyrosine, in particular phenylalanine or alanine, comprising a methyl group attached to the α-amino group;

Px is alanine, valine, leucine, isoleucine, phenylalanine or tyrosine, in particular valine or phenylalanine, coupled with its α-carboxylic acid group to the hydroxyl group of P2, forming an ester bond;

R is hydrogen or a C1-8 aliphatic or aromatic alkyl group forming an amid bond or a carbamate bond with the amino group to which it is attached.

Especially, in the Ahp-cyclodepsipeptide capable of binding to human HTRA2 and reducing or inhibiting its protease activity P1 is valine;

P2 is (3-OH)-phenylalanine or (3-OH)-leucine;

P3 is alanine or phenylalanine;

P4 is alanine or is absent;

P1' is 5-hydroxy-norvaline forming a 3-amino-6-hydroxy-2-piperidone unit with the α-amino group of P2';

P2' is leucine;

P3' is phenylalanine comprising a methyl group attached to the α-amino group;

Px is valine coupled with its α-carboxylic acid group to the hydroxyl group of P2, forming an ester bond;

R is hydrogen or a C1-8 aliphatic or aromatic alkyl group forming an amid bond or a carbamate bond with the amino group to which it is attached.

The Ahp-cyclodepsipeptide capable of binding to human HTRA3 and reducing or inhibiting its protease activity in particular has the following features:

P1 is an amino acid with a C1-3 aliphatic hydrophobic side chain;

P2 is an amino acid with a hydroxyl group in the aliphatic or aromatic side chain;

P3 is an amino acid with an aliphatic hydrophobic side chain;

P4 is an amino acid with an aliphatic hydrophobic side chain or is absent;

P1' is 5-hydroxy-norvaline forming a 3-amino-6-hydroxy-2-piperidone unit with the α-amino group of P2';

P2' is an amino acid with an aliphatic hydrophobic side chain;

P3' is an amino acid with an aromatic hydrophobic side chain comprising a methyl group attached to the α-amino group;

Px is an amino acid with a hydrophobic side chain coupled with its α-carboxylic acid group to the hydroxyl group of P2, forming an ester bond;

R is hydrogen or a C1-15 aliphatic or aromatic alkyl group forming an amid bond or a carbamate bond with the amino group to which it is attached.

In certain embodiments, in the Ahp-cyclodepsipeptide capable of binding to human HTRA3 and reducing or inhibiting its protease activity P1 is alanine, valine, homoalanine or an α-amino acid with a cyclopropyl group as side chain, in particular valine;
P2 is threonine, (3-OH)-phenylalanine or (3-OH)-leucine, in particular (3-OH)-leucine;
P3 is alanine or valine, in particular alanine;
P4 is alanine or valine, in particular alanine, or is absent;
P1' is 5-hydroxy-norvaline forming a 3-amino-6-hydroxy-2-piperidone unit with the α-amino group of P2';
P2' is leucine or isoleucine, in particular leucine;
P3' is phenylalanine or tyrosine, in particular phenylalanine, comprising a methyl group attached to the α-amino group;
Px is alanine, valine, leucine, isoleucine, phenylalanine or tyrosine, in particular valine or phenylalanine, coupled with its α-carboxylic acid group to the hydroxyl group of P2, forming an ester bond;
R is hydrogen or a C1-8 aliphatic or aromatic alkyl group forming an amid bond or a carbamate bond with the amino group to which it is attached.

Especially, in the Ahp-cyclodepsipeptide capable of binding to human HTRA3 and reducing or inhibiting its protease activity
P1 is valine;
P2 is threonine, (3-OH)-phenylalanine or (3-OH)-leucine, in particular (3-OH)-leucine;
P3 is alanine;
P4 is alanine or is absent;
P1' is 5-hydroxy-norvaline forming a 3-amino-6-hydroxy-2-piperidone unit with the α-amino group of P2';
P2' is leucine;
P3' is phenylalanine comprising a methyl group attached to the α-amino group;
Px is valine or phenylalanine, in particular valine, coupled with its α-carboxylic acid group to the hydroxyl group of P2, forming an ester bond;
R is hydrogen or a C1-8 aliphatic or aromatic alkyl group forming an amid bond or a carbamate bond with the amino group to which it is attached.

In a further aspect, the present invention is directed to Ahp-cyclodepsipeptides which comprise an α-amino acid with a cyclopropyl group as side chain at position P1 ("cyclopropyl-Ahp-cyclodepsipeptides"). The cyclopropyl-Ahp-cyclodepsipeptide in particular has the following formula

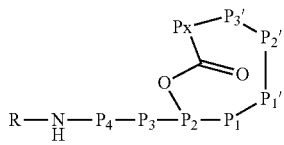

wherein
P1 is an α-amino acid with a cyclopropyl group as side chain;
P2 is an amino acid with a hydroxyl group in the side chain;
P3 is any amino acid or is absent;
P4 is any amino acid or is absent;
P1' is 5-hydroxy-norvaline forming a 3-amino-6-hydroxy-2-piperidone unit with the α-amino group of P2';
P2' is any amino acid;
P3' is an amino acid with a hydrophobic side chain comprising a methyl group attached to the α-amino group;
Px is any amino acid coupled with its α-carboxylic acid group to the hydroxyl group of P2, forming an ester bond; and
R is hydrogen or a chemical group.

P2, P3, P4, P2', P3' and Px each may be a natural or a non-natural amino acid. All these amino acids may be selected independently of each other.

P1 of the cyclopropyl-Ahp-cyclodepsipeptide is an L-α-amino acid having the formula

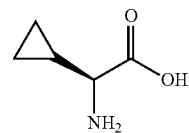

In certain embodiments of the cyclopropyl-Ahp-cyclodepsipeptide, P2 is an amino acid with an aliphatic side chain comprising a hydroxyl group. P2 may be selected from the group consisting of threonine, (3-OH)-phenylalanine, (3-OH)-leucine, tyrosine and serine, especially threonine, (3-OH)-phenylalanine and (3-OH)-leucine. In particular, P2 is threonine.

In certain embodiments of the cyclopropyl-Ahp-cyclodepsipeptide, P3 is an amino acid with an aliphatic or aromatic side chain. In particular, P3 may be an amino acid with a C1-3 aliphatic hydrophobic side chain. In these embodiments, P3 may be selected from the group consisting of alanine and valine, especially alanine. Furthermore, P3 may be an amino acid with an aromatic side chain, especially phenylalanine or a phenylalanine derivative. Specific phenylalanine derivatives are homophenylalanine and phenylalanines wherein the phenyl ring is substituted with a halogen or a nitrile group, especially p-chlorophenylalanine, m-chlorophenylalanine, m-fluorophenylalanine and m-cyanophenylalanine. In particular, P3 is alanine or m-fluorophenylalanine.

In certain embodiments of the cyclopropyl-Ahp-cyclodepsipeptide, P4 is an amino acid with a hydrophobic side chain, especially with an aliphatic hydrophobic side chain, in particular with a C1-3 aliphatic hydrophobic side chain. P4 may be selected from the group consisting of alanine, valine, leucine and isoleucine, especially alanine and valine. In particular, P4 is alanine. Alternatively, P4 is absent.

In certain embodiments of the cyclopropyl-Ahp-cyclodepsipeptide, P2' is an amino acid with an aromatic and/or hydrophilic side chain. P2' may be selected from the group consisting of glutamic acid, aspartic acid, glutamine, asparagine, arginine, phenylalanine, homophenylalanine and phenylalanine wherein the phenyl ring is substituted with a halogen or a nitrile group. P2' may in particular be glutamic acid, asparagine, phenylalanine, p-chlorophenylalanine, p-bromophenylalanine, m-fluorophenylalanine, m-cyanophenylalanine or an α-amino acid with a —CH$_2$CH$_2$CH$_2$NHC(=O)NH$_2$ group as side chain. In particular, P2' is p-chlorophenylalanine or phenylalanine. In further embodiments, P2' is an amino acid with a hydrophobic side chain, especially with an aliphatic hydrophobic side chain. In these embodiments, P2' may be selected from the group consisting of alanine, valine, leucine, isoleucine, phenylalanine, tyrosine and tryptophan, especially leucine, isoleucine and phenylalanine, in particular leucine.

In certain embodiments of the cyclopropyl-Ahp-cyclodepsipeptide, P3' is an amino acid with an aromatic hydrophobic side chain comprising a methyl group attached to the α-amino group. P3' may be selected from the group consisting of alanine, valine, leucine, isoleucine, phenylalanine, tyrosine and tryptophan, especially phenylalanine, tyrosine and alanine. In particular, P3' is phenylalanine.

In certain embodiments of the cyclopropyl-Ahp-cyclodepsipeptide, Px is an amino acid with a hydrophobic side chain, especially with an aliphatic hydrophobic side chain, in particular with a C1-3 aliphatic hydrophobic side chain. Px may be selected from the group consisting of alanine, valine, leucine, isoleucine, phenylalanine, tyrosine and tryptophan, especially alanine, valine and phenylalanine. In particular, Px is valine.

In certain embodiments of the cyclopropyl-Ahp-cyclodepsipeptide, R is hydrogen or a C1-15, especially C1-8, aliphatic or aromatic alkyl group forming an amide bond or a carbamate bond with the amino group to which it is attached. In certain embodiments, R is hydrogen. In other embodiments, R is a protecting group such as carboxybenzyl.

In further embodiments, R is an acyl group, especially a C1-8 acyl group such as acetyl, propionyl, butyryl and benzoyl. In further embodiments, R includes or consists of one or more amino acids, especially one or two amino acids, named R5 and R6, attached via peptide bonds to R4. These further amino acids may be any amino acids, and in particular R5 and/or R6 may be amino acids with a polar side chain. In these embodiments, R may further include a C1-15 aliphatic or aromatic alkyl group or a protecting group attached to the N terminus of these further amino acids.

The cyclopropyl-Ahp-cyclodepsipeptide may be obtainable or obtained by the method for synthesizing an Ahp-cyclodepsipeptide as described herein.

In specific embodiments of the cyclopropyl-Ahp-cyclodepsipeptide
  P1 is an α-amino acid with a cyclopropyl group as side chain;
  P2 is threonine or (3-OH)-leucine, in particular threonine;
  P3 is alanine, valine, phenylalanine or phenylalanine wherein the phenyl group is substituted with halogen or a cyano group, in particular alanine, p-chlorophenylalanine, m-chlorophenylalanine, m-fluorophenylalanine and m-cyanophenylalanine;
  P4 is alanine or valine, in particular alanine;
  P1' is 5-hydroxy-norvaline forming a 3-amino-6-hydroxy-2-piperidone unit with the α-amino group of P2';
  P2' is leucine, phenylalanine, phenylalanine wherein the phenyl group is substituted with halogen or a cyano group, glutamic acid, asparagine or an α-amino acid with a —CH$_2$CH$_2$CH$_2$NHC(=O)NH$_2$ group as side chain, in particular leucine, phenylalanine, p-chlorophenylalanine, p-bromophenylalanine, m-fluorophenylalanine, m-cyanophenylalanine or an α-amino acid with a —CH$_2$CH$_2$CH$_2$NHC(=O)NH$_2$ group as side chain;
  P3' is phenylalanine or tyrosine, in particular phenylalanine, comprising a methyl group attached to the α-amino group;
  Px is alanine or valine, in particular valine, coupled with its α-carboxylic acid group to the hydroxyl group of P2, forming an ester bond;
  R is hydrogen or a C1-8 aliphatic or aromatic alkyl group forming an amid bond or a carbamate bond with the amino group to which it is attached.

In certain embodiments of the cyclopropyl-Ahp-cyclodepsipeptide,
  P1 is an L-α-amino acid with a cyclopropyl group as side chain;
  P2 is threonine;
  P3 is alanine;
  P4 is alanine;
  P1' is 5-hydroxy-norvaline forming a 3-amino-6-hydroxy-2-piperidone unit with the α-amino group of P2';
  P2' is leucine, phenylalanine, p-chlorophenylalanine, p-bromophenylalanine, m-fluorophenylalanine, m-cyanophenylalanine or an α-amino acid with a —CH$_2$CH$_2$CH$_2$NHC(=O)NH$_2$ group as side chain, in particular phenylalanine, p-chlorophenylalanine or an α-amino acid with a —CH$_2$CH$_2$CH$_2$NHC(=O)NH$_2$ group as side chain, especially p-chlorophenylalanine;
  P3' is phenylalanine comprising a methyl group attached to the α-amino group;
  Px is valine, coupled with its α-carboxylic acid group to the hydroxyl group of P2, forming an ester bond;
  R is hydrogen or a C1-8 aliphatic or aromatic alkyl group forming an amid bond or a carbamate bond with the amino group to which it is attached, such as a carboxybenzyl group.

In further embodiments of the cyclopropyl-Ahp-cyclodepsipeptide,
  P1 is an L-α-amino acid with a cyclopropyl group as side chain;
  P2 is threonine;
  P3 is m-chlorophenylalanine, m-fluorophenylalanine or m-cyanophenylalanine;
  P4 is alanine;
  P1' is 5-hydroxy-norvaline forming a 3-amino-6-hydroxy-2-piperidone unit with the α-amino group of P2';
  P2' is phenylalanine or p-chlorophenylalanine;
  P3' is phenylalanine comprising a methyl group attached to the α-amino group;
  Px is valine, coupled with its α-carboxylic acid group to the hydroxyl group of P2, forming an ester bond;
  R is hydrogen or a C1-8 aliphatic or aromatic alkyl group forming an amid bond or a carbamate bond with the amino group to which it is attached, such as a carboxybenzyl group.

In these embodiments, P3 especially is m-fluorophenylalanine and P2' is p-chlorophenylalanine.

The cyclopropyl-Ahp-cyclodepsipeptide are especially suitable for inhibiting HTRA1 protease.

The Therapeutic Use of the Ahp-Cyclodepsipeptides

In a further aspect, the present invention provides an Ahp-cyclodepsipeptide for use in the treatment of a HTRA-dependent disease, wherein the Ahp-cyclodepsipeptide has the following formula

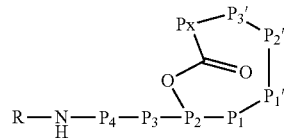

wherein
  P1 is an amino acid with an aliphatic hydrophobic side chain;
  P2 is an amino acid with a hydroxyl group in the side chain;
  P3 is any amino acid or is absent;
  P4 is any amino acid or is absent;

P1' is 5-hydroxy-norvaline forming a 3-amino-6-hydroxy-2-piperidone unit with the α-amino group of P2';
P2' is any amino acid;
P3' is an amino acid with a hydrophobic side chain comprising a methyl group attached to the α-amino group;
Px is any amino acid coupled with its α-carboxylic acid group to the hydroxyl group of P2, forming an ester bond; and
R is hydrogen or a chemical group.

Without indicating the amino group of the N terminus and the ester bond between R2 and Rx, the formula of the Ahp-cyclodepsipeptide may be written as follows:

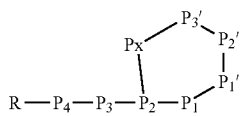

In specific embodiments,
P1 is an amino acid with an aliphatic hydrophobic side chain;
P2 is an amino acid with a hydroxyl group in the side chain;
P3 is an amino acid with a hydrophobic side chain or is absent;
P4 is an amino acid with an aliphatic hydrophobic side chain or is absent;
P1' is 5-hydroxy-norvaline forming a 3-amino-6-hydroxy-2-piperidone unit with the α-amino group of P2';
P2' is an amino acid with a hydrophobic side chain;
P3' is an amino acid with a hydrophobic side chain comprising a methyl group attached to the α-amino group;
Px is an amino acid with a hydrophobic side chain coupled with its α-carboxylic acid group to the hydroxyl group of P2, forming an ester bond;
R is hydrogen or a chemical group.

In particular, the Ahp-cyclodepsipeptide is as defined herein.

The HTRA-dependent disease especially is a disease wherein a reduced activity of one or more HTRA proteases is beneficial. In certain embodiments, the HTRA-dependent disease is a disease wherein a reduced HTRA1 activity is beneficial. In particular, it may be a disease based on deregulated HTRA1 hyperactivity. Exemplary diseases wherein a reduced HTRA1 activity is beneficial include macular degeneration, in particular age-related macular degeneration, polypoidal choroidal vasculopathy, arthritis such as osteoarthritis and rheumatoid arthritis, osteoporosis, intervertebral disc degeneration and cancer. The cancer is in particular a cancer comprising cancer cells having an increased HTRA1 activity compared to normal cells of the same tissue, such as an increase HTRA1 expression level, for example cancer cells with HTRA1 overexpression. Examples of such cancers include fast migrating and invading gliomas and papillary thyroid carcinomas. For treatment of these diseases, an Ahp-cyclodepsipeptide is used which is capable of binding to human HTRA1 and reducing or inhibiting its protease activity, as described herein. The cyclopropyl-Ahp-cyclodepsipeptides as described herein are especially suitable for use in the treatment of a disease wherein a reduced HTRA1 activity is beneficial.

In further embodiments, the HTRA-dependent disease is a disease wherein a reduced HTRA2 activity is beneficial. In particular, it may be a disease based on deregulated HTRA2 hyperactivity. Exemplary diseases wherein a reduced HTRA2 activity is beneficial include Parkinson's disease and cancer. The cancer is in particular a cancer comprising cancer cells having an increased HTRA2 activity compared to normal cells of the same tissue, such as an increase HTRA2 expression level, for example cancer cells with HTRA2 overexpression. For treatment of these diseases, an Ahp-cyclodepsipeptide is used which is capable of binding to human HTRA2 and reducing or inhibiting its protease activity, as described herein.

In further embodiments, the HTRA-dependent disease is a disease wherein a reduced HTRA3 activity is beneficial. In particular, it may be a disease based on deregulated HTRA3 hyperactivity. Exemplary diseases wherein a reduced HTRA3 activity is beneficial include infertility, pregnancy disorders such as pre-eclampsia and intra uterine growth cancer, and cancer. The cancer is in particular a cancer comprising cancer cells having an increased HTRA3 activity compared to normal cells of the same tissue, such as an increase HTRA3 expression level, for example cancer cells with HTRA3 overexpression. For treatment of these diseases, an Ahp-cyclodepsipeptide is used which is capable of binding to human HTRA3 and reducing or inhibiting its protease activity, as described herein.

The Ahp-cyclodepsipeptide is in particular used in the treatment of human patients. In certain embodiments, the Ahp-cyclodepsipeptide is administered as part of a pharmaceutical composition.

The present invention also provides a method for treating a patient afflicted with a HTRA-dependent disease, comprising the step of administering the patient in need thereof a therapeutically effective amount of an Ahp-cyclodepsipeptide as defined herein. The feature disclosed herein with respect to a Ahp-cyclodepsipeptide for use in the treatment of a HTRA-dependent disease likewise also apply to the method for treating a patient afflicted with a HTRA-dependent disease.

Inhibition of HTRA protease activity

In a further aspect, the present invention provides a method for reducing or inhibiting the protease activity of a HTRA protease, comprising the step of contacting the HTRA protease with an Ahp-cyclodepsipeptide having the following formula

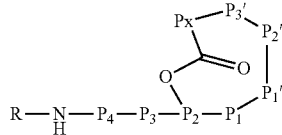

wherein
P1 is an amino acid with an aliphatic hydrophobic side chain;
P2 is an amino acid with a hydroxyl group in the side chain;
P3 is any amino acid or is absent;
P4 is any amino acid or is absent;
P1' is 5-hydroxy-norvaline forming a 3-amino-6-hydroxy-2-piperidone unit with the α-amino group of P2';
P2' is any amino acid;
P3' is an amino acid with a hydrophobic side chain comprising a methyl group attached to the α-amino group;

Px is any amino acid coupled with its α-carboxylic acid group to the hydroxyl group of P2, forming an ester bond;

R is hydrogen or a chemical group.

The HTRA protease in particular is selected from the group consisting of human HTRA1, human HTRA2 and human HTRA3.

In certain embodiments, the HTRA protease is HTRA1 and the Ahp-cyclodepsipeptide is an Ahp-cyclodepsipeptide capable of binding to human HTRA1 and reducing or inhibiting its protease activity as described herein. In particular, all embodiments and features of the Ahp-cyclodepsipeptide capable of binding to human HTRA1 and reducing or inhibiting its protease activity described herein also apply to the method for reducing or inhibiting the protease activity of a HTRA protease. In certain embodiments, the Ahp-cyclodepsipeptide is a cyclopropyl-Ahp-cyclodepsipeptide as described herein.

In certain embodiments, the HTRA protease is HTRA2 and the Ahp-cyclodepsipeptide is an Ahp-cyclodepsipeptide capable of binding to human HTRA2 and reducing or inhibiting its protease activity as described herein. In particular, all embodiments and features of the Ahp-cyclodepsipeptide capable of binding to human HTRA2 and reducing or inhibiting its protease activity described herein also apply to the method for reducing or inhibiting the protease activity of a HTRA protease.

In certain embodiments, the HTRA protease is HTRA3 and the Ahp-cyclodepsipeptide is an Ahp-cyclodepsipeptide capable of binding to human HTRA3 and reducing or inhibiting its protease activity as described herein. In particular, all embodiments and features of the Ahp-cyclodepsipeptide capable of binding to human HTRA3 and reducing or inhibiting its protease activity described herein also apply to the method for reducing or inhibiting the protease activity of a HTRA protease.

In specific embodiments, the method for reducing or inhibiting the protease activity of a HTRA protease is not performed in the human body, especially not performed in the human or animal body. Especially, the method for reducing or inhibiting the protease activity of a HTRA protease is an in vitro method.

Screening Method

In a further aspect, the present invention provides a method of screening for an Ahp-cyclodepsipeptide capable of reducing or inhibiting the protease activity of a HTRA protease, comprising the steps of synthesizing an Ahp-cyclodepsipeptide using the method for synthesizing an Ahp-cyclodepsipeptide as described herein, contacting an HTRA protease with the Ahp-cyclodepsipeptide, and determining the protease activity of the HTRA protease in the presence of the Ahp-cyclodepsipeptide.

The HTRA protease in particular is selected from the group consisting of human HTRA1, human HTRA2 and human HTRA3. Any method suitable for determining the protease activity of the HTRA protease may be used in the screening method. The protease activity of the HTRA protease may be determined directly or indirectly. For example, the HTRA protease may be incubated with a substrate in the presence of the Ahp-cyclodepsipeptide for a suitable time and then the presence or amount of the substrate or of a protease product may be determined. For detecting the amount of the substrate or product of the HTRA protease, a substrate with a detectable label may be used, in particular a detectable label which changes upon cleavage by the HTRA protease. Suitable examples are chromogenic substrates which change in their adsorption at specific a wavelength upon cleavage of the substrate, such as para-nitroaniline. Furthermore, also indirect assays may be used to determine the protease activity of the HTRA protease, such as cell-based assays. For example, cells which survival or proliferation is dependent on the activity of the HTRA protease may be cultivated with the HTRA protease in the presence and absence of the Ahp-cyclodepsipeptide and the difference in cell number between the samples with and without the Ahp-cyclodepsipeptide after cultivation may be indicative for the activity of the HTRA protease in the presence of the Ahp-cyclodepsipeptide.

FIGURES

FIG. 1 shows the chemical structure of and its corresponding binding mode.

Figure 2:
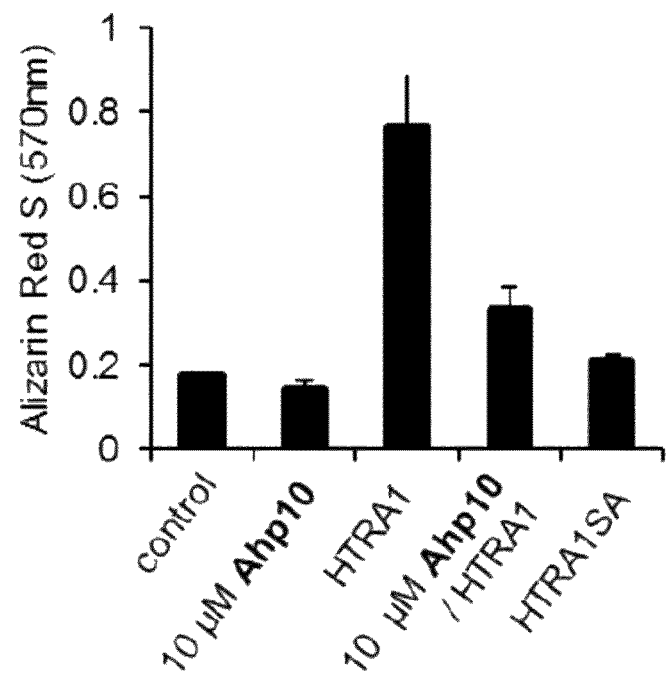

FIG. 2 shows the cell-based evaluation of HTRA1 inhibition potency of Ahp10. Alizarin Red S staining of HTRA1-mediated biomineralization of mesenchymal stem cells in absence or presence of 10 μM Ahp10 as well as HTRA1 or a catalytically inactive mutant HTRA1SA. Error bars indicate standard deviation of three independent measurements.

EXAMPLES

Example 1: Chemical Synthesis of Ahp-Cyclodepsipeptides

1. General Information

Reagents

All reagents were purchased from Iris Biotech, Biosolve Chemicals, Carbolution Chemicals, ABCR, Novabiochem, Sigma Aldrich, TCI Chemicals, Bernd Kraft or VWR Chemicals and were used without further purification.

Reversed-Phase Liquid Chromatography Electrospray Ionization Mass Spectrometry (LC-MS)

Reaction control analyses were performed on a LC-MS system from Thermo Scientific. The system consisted of a Thermo Scientific Accela (peak detection at 210 nm) equipped with an Eclipse XDB-C18 5 μm column (both from Agilent) and a Thermo Scientific LCQ Fleet ESI-MS. For analysis, a linear gradient of solvent B (0.1% formic acid in acetonitrile) in solvent A (0.1% formic acid in water) at flow rate of 1 mL min$^{-1}$ and the following gradient program: 0 min./10% B→1 min./10% B→10 min./100% B→12 min./100% B→15 min./10% B was used.

Preparative Reversed-Phase High Performance Liquid Chromatography (Prep HPLC)

Compound purification was achieved by preparative reversed-phase HPLC using the Prominence UFLC system from Shimadzu (peak detection at 210 nm). The system was equipped with a reversed-phase column Luna® 5 μm C18 (2), 100×21.20 mm. A linear gradient acetonitrile in water (0.1% TFA) at a flow rate of 25 mL min$^{-1}$ was used that adapted for each purification application.

Nuclear Magnetic Resonance Spectroscopy (NMR)

Nuclear magnetic resonance (NMR) spectra were recorded on an Avance II 400 (400 MHz for $^1$H- and 100 MHz for $^{13}$C-NMR) or an Avance II 700 (400 MHz for $^1$H- and 176 MHz for $^{13}$C-NMR) machine. $^1$H NMR spectra are reported in the following manner: chemical shifts (δ) in ppm calculated with reference to the residual signals of undeuterated solvent, multiplicity (s, singlet; d, doublet; t, triplet; dd, doublet of doublet; dt, doublet of triplet; td, triplet of doublet; m, multiplet), coupling constants (J) in Hertz (Hz), and number of protons (H).

2. Synthesis of Solid Phase Building Block

Synthesis of N-(9-Fluorenylmethoxycarbonyl)-(L)-5-hydroxy-norvaline-1-allyl ester (SI-1)

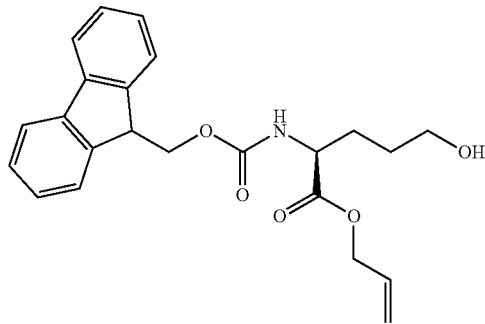

SI-1

N-(9-Fluorenylmethoxycarbonyl)-(L)-glutamic acid-1-allyl ester (1.00 g, 2.44 mmol, 1 eq) was dissolved in anhydrous THF (150 mL) under an argon atmosphere. Triethyl amine (1.01 mL, 7.33 mmol, 3 eq) and isobutyl chloroformiate (1.26 mL, 9.77 mmol, 4 eq) were added at room temperature. The resulting suspension was stirred for 15 minutes. Sodium borohydride (557 mg, 14.66 mmol, 6 eq) was dissolved in water (50 mL) and was slowly added. The resulting slightly cloudy solution was stirred for further 15 min. The reaction was quenched by addition of 1 M aq. potassium hydrogen sulfate solution (50 mL) and the product was extracted with DCM (3×100 mL). The combined organic phases were dried over magnesium sulfate and the crude product was purified by flash column chromatography (ethyl acetate:cyclohexane (1:1)->dichloromethane: methanol (50:1)).

Yield: 695 mg (1.76 mmol, 72%) as white solid.

TLC (ethyl acetate:cyclohexane (1:1)): $R_f$=0.33; LC-MS (ESI): $t_R$=8.65 min; m/z=395.8 $[M+H]^+$, 418.1 $[M+Na]^+$, 377.7 $[M+H-OH]^+$, 337.7 $[M+H-OAll]^+$, calcd. for $C_{23}H_{25}NO_5$: 395.17.

$^1$H NMR (400 MHz, DMSO-d6) δ 7.90 (d, J=7.5 Hz, 2H), 7.83 (d, J=7.8 Hz, 1H), 7.73 (dd, J=7.4, 2.2 Hz, 2H), 7.42 (t, J=7.4 Hz, 2H), 7.34 (t, J=7.4 Hz, 2H), 5.95-5.85 (m, 1H), 5.31 (dq, J=17.3, 1.8 Hz, 1H), 5.21 (dt, J=10.5, 1.6 Hz, 1H), 4.59 (d, J=5.3 Hz, 2H), 4.52-4.41 (m, 1H), 4.36-4.17 (m, 3H), 4.13-4.04 (m, 1H), 3.40 (tt, J=6.4, 3.1 Hz, 2H), 1.85-1.77 (m, 1H), 1.70-1.61 (m, 1H), 1.57-1.40 (m, 2H).

$^{13}$C NMR (101 MHz, DMSO) δ 172.14, 156.12, 143.79, 140.70, 132.38, 127.61, 127.03, 125.23, 120.09, 117.66, 65.64, 64.69, 60.00, 53.81, 46.62, 28.83, 27.44.

3. General Methods for Solid Phase Synthesis

Method A: Resin Loading

N-(9-Fluorenylmethoxycarbonyl)-(L)-5-hydroxy-norvaline-1-allyl ester (103 mg, 0.26 μmol, 1 eq) was dissolved in anhydrous DCM and pyridine (63 μL, 0.78 mmol, 3 eq) was added. The loading solution was added under inert gas to a chlorotrityl resin (1 g, max. loading: 1.6 mmol g$^{-1}$) and the resulting suspension was gently shaken for 72 h. The solution was removed and the resin was washed with DMF (2×1 min). The resin was washing with a DCM/MeOH/DIPEA (85:10:5, 3×15 min.) solution. The resin was washed with DMF (3×1 min) and DCM (3×1 min).

Method B: Determination of Loading Efficiency

An aliquot of the loaded resin (~10 mg) was treated with freshly prepared 20% piperidine/DMF solution (5 mL) for 20 min. The solution was separated from the resin and the UV absorption of the solution was measured at a wavelength of 301 nm by a UV spectrophotometer. The loading was determined from the measured parameters via the following equation: $β=A·V/ε·d·m·F$ [mmol/g]

A is the absorption at 301 nm, V the total volume, ε the extinction coefficient of cleaved Fmoc, d the thickness of the cuvette, m the mass of the resin and F the dilution factor (1 unless further dilutions were taken).

Method C: Amino Acid Coupling

The amino acid (4 eq) and HBTU (4 eq) were dissolved in 0.2 M HOBt in DMF (5.5 mL). This solution and DIPEA (4 eq) were added to the resin and the resulting suspension was shaken for 45 min. The solution was separated from the resin was washed with DMF (3×1 min).

Method D: Fmoc Deprotection

A solution of 40% piperidine in DMF (6 mL) was added to resin and the resulting suspension was shaken for 3 min. The piperidine solution was removed and resin was treated with 20% piperidine in DMF for another 12 min (6 mL). The deprotection solution was removed and the resin was washed with DMF (6×1 min).

Method E: Esterification

The corresponding amino acid (10 eq) was dissolved in DCM (4 mL) and DIPEA (10 eq) was added. DMAP (0.5 eq) was dissolved in DCM (0.75 mL) and both solutions and DIC (10 eq) were added to the resin and the resulting suspension was shaken for 60 min at 40° C. The solution was removed and the resin was washed with DCM (3×1 min). The whole esterification procedure was repeated four more times. The resin was washed with DMF (5×1 min).

Method F: Amino Acid Coupling on Methylated Amino Groups

PyBrop (4 eq) and amino acid (4 eq) was dissolved in DCM (5 mL). The resulting solution and DIPEA (4 eq) were added to the resin. The resulting suspension was shaken for 60 min at 40° C. The solution was discarded and the resin was washed with DCM (3×1 min). The procedure was repeated five times. The resin was washed with DMF (5×1 min).

Method G: Allyl Deprotection

The resin was washed five times with anhydrous DCM under inert gas and a solution of tetrakis(triphenylphosphine)palladium(0) (0.5 eq) and morpholine (24 eq) in anhydrous DCM (5.5 mL) was added. The resulting suspension was shaken for two hours.

The solution was removed and the resin was washed with DCM (3×1 min), DMF (3×1 min) and NMP (3×1 min). The procedure was completed by washing steps with a 0.02 M solution of Et2NCS2Na in NMP (3×5 min), NMP (3×1 min), DMF (3×1 min) and DCM (3×1 min).

Method H: Peptide Cyclization

HBTU (4 eq), HOBt (4 eq) and DIPEA (4 eq) were dissolved in DMF (5 mL). The solution was added to the resin and the resulting suspension was shaken overnight. The cyclization solution was removed and the resin was washed with DMF (3×1 min), NMP (3×1 min), DMF (3×1 min) and DCM (3×1 min).

Method I: Cleavage from Resin

The resin was treated with a solution of TFA/triisopropylsilane/H2O (95:2.5:2.5, 9 mL) for 2 h. The cleavage solution was transferred in a flask and the resin was washed with DCM (3×1 min). All solutions were combined in the flask. From the resulting solution, DCM was evaporated and TFA was co-evaporated with toluene under reduce pressure to dryness. The residue was dried at high vacuum.

Method J: Dess-Martin Oxidation

The purified Ahp-cyclodepsipeptide precursor (1 eq) was dissolved in DCM (10 mL) and Dess-Martin periodinane (1.5 eq) was added. The slightly turbid solution was stirred for 1 h. The solution was evaporated under reduce pressure and the residue was dissolved in acetonitrile/water (1:1, 5 mL) and stirred overnight.

4. General Synthesis Procedure for Ahp-Cyclodepsipeptides

Fmoc-Hnv-OAll was loaded on chlorotrityl resin according to method A. The resin loading was determined using method B ($\beta$=0.2 mmol g−1). 1000 mg resin (0.2 mmol) were used for synthesis. The first four amino acids were coupled by alternatingly using method C and method D for Fmoc deprotection. This step was followed by the esterification with a Fmoc-protected amino acid using method E. The Fmoc group was cleaved (method D) and the Fmoc-protected and N-methylated amino acid was coupled (method C). Fmoc deprotection (method D) delivered the starting material for coupling of the last amino acid via method F, followed by Fmoc deprotection (method D). The allyl ester was cleaved with method G. The peptide was cyclized using method H and was cleaved according to method I. The crude product was purified by preparative reversed-phase HPLC. The residue was oxidized according to method J, followed by an HPLC purification, thereby delivering the desired Ahp-cyclodepsipeptide.

Example 2: Synthesis of Specific Ahp-Cyclodepsipeptides

Ahp1 (18)

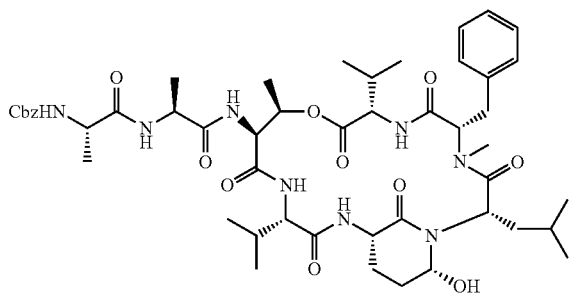

Ahp1 (18) was synthesized via the 'general synthesis procedure for Ahp-cyclodepsipeptides'.

Yield: 9.9 mg (10.3 µmol, 5.2%) as a white solid.

$^1$H NMR (400 MHz, DMSO-d6): δ 8.18 (d, J=9.4 Hz, 1H), 8.04 (d, J=7.8 Hz, 1H), 7.87 (d, J=9.6 Hz, 1H), 7.51-7.10 (m, 12H), 5.98 (t, J=1.7 Hz, 1H), 5.65-5.55 (m, 1H), 5.08-5.02 (m, 3H), 4.89 (s, 1H), 4.78-4.70 (m, 2H), 4.61-4.51 (m, 1H), 4.52-4.43 (m, 1H), 4.44-4.34 (m, 1H), 4.29 (dd, J=9.5, 4.0 Hz, 1H), 4.08 (p, J=7.2 Hz, 1H), 2.92-2.74 (m, 1H), 2.74 (s, 3H), 2.55 (t, J=5.6 Hz, 1H), 2.21-2.16 (m, 1H), 2.12-2.03 (m, 1H), 1.75-1.72 (m, 3H), 1.60-1.42 (m, 1H), 1.26-1.19 (m, 12H), 0.87 (dd, J=6.7, 5.2 Hz, 3H), 0.85-0.75 (m, 6H), 0.74 (d, J=6.9 Hz, 3H), 0.67 (d, J=6.6 Hz, 3H), 0.43 (d, J=6.5 Hz, 3H), 0.33-0.21 (m, 1H).

LC-MS (ESI): $t_R$=8.27 min; m/z=962.8 [M+H]$^+$, 945.0 [M+H−H$_2$O]$^+$, 985.4 [M+Na]$^+$, calcd. for $C_{49}H_{70}N_8O_{12}$: 962.51.

Ahp2 (19)

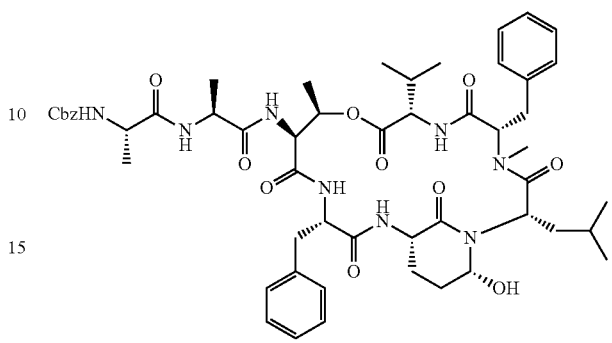

Ahp2 (19) was synthesized via the 'general synthesis procedure for Ahp-cyclodepsipeptides'.

Yield: 1.1 mg (1.1 µmol, 0.6%) as a white solid.

$^1$H NMR (700 MHz, DMSO-d6): δ 8.86 (d, J=9.6 Hz, 1H), 8.51 (d, J=4.1 Hz, 1H), 8.49 (d, J=7.5 Hz, 1H), 8.34 (d, J=9.6 Hz, 1H), 7.33-7.03 (m, 17H), 5.60 (d, J=5.4 Hz, 1H), 5.43 (t, J=5.3 Hz, 1H), 5.09-5.06 (m, 1H), 4.89 (s, 2H), 4.65 (dd, J=9.7, 3.3 Hz, 1H), 4.58-4.3 (m, 1H), 4.51-4.41 (m, 3H), 4.30-4.24 (m, 2H), 4.04 (q, J=7.1 Hz, 1H), 3.81 (dd, J=14.1, 2.8 Hz, 1H), 2.91-2.85 (m, 1H), 2.83 (dd, J=14.1, 5.0 Hz, 1H), 2.74 (s, 3H), 2.62-2.57 (m, 1H), 2.33-2.25 (m, 1H), 1.80-1.76 (m, 1H), 1.68-1.60 (m, 1H), 1.54-1.44 (m, 2H), 1.18 (dd, J=7.2, 2.6 Hz, 6H), 1.02 (d, J=6.2 Hz, 3H), 0.93 (td, J=14.0, 13.5, 3.3 Hz, 1H), 0.88-0.82 (m, 1H), 0.79 (d, J=6.9 Hz, 3H), 0.69 (dd, J=9.1, 6.7 Hz, 6H), 0.62 (d, J=6.7 Hz, 3H), −0.67 (t, J=12.4 Hz, 1H).

$^{13}$C NMR (176 MHz, DMSO-d6): δ 202.86, 173.87, 173.51, 172.11, 171.71, 171.64, 171.04, 170.80, 169.90, 166.46, 155.85, 139.40, 137.45, 137.34, 130.39, 129.32, 129.12, 128.52, 127.90, 127.55, 126.80, 80.43, 73.69, 65.83, 62.86, 60.22, 58.87, 56.09, 55.38, 53.87, 50.95, 49.66, 47.61, 47.37, 37.45, 33.74, 31.39, 30.05, 29.21, 26.81, 23.86, 23.77, 21.24, 20.08, 19.97, 19.83, 17.24, 16.42, 15.40, 14.56, 1.63.

LC-MS (ESI): $t_R$=8.77 min; m/z=1011.6 [M+H]$^+$, 993.0 [M+H−H$_2$O]$^+$, 1033.4 [M+Na]$^+$, calcd. for $C_{53}H_{70}N_8O_{12}$: 1010.51.

Ahp3 (20)

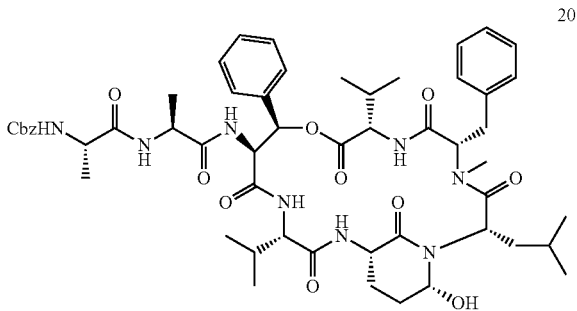 [SMILES: CC(C)C[C@H]1C(=O)N(C)[C@@H](Cc2ccccc2)C(=O)N[C@@H](C(C)C)C(=O)O[C@H](c2ccccc2)[C@H](NC(=O)[C@H](C)NC(=O)[C@H](C)NC(=O)OCc2ccccc2)C(=O)N[C@@H](C(C)C)C(=O)N[C@H]2CC[C@@H](O)N1C2=O]

Ahp3 (20) was synthesized via the 'general synthesis procedure for Ahp-cyclodepsipeptides'.

Yield: 1.0 mg (1.0 μmol, 0.5%) as a white solid.

$^1$H NMR (400 MHz, DMSO-d6): δ 8.90 (d, J=9.6 Hz, 1H), 8.46 (d, J=3.9 Hz, 1H), 8.39 (d, J=9.6 Hz, 1H), 7.98 (d, J=7.6 Hz, 1H), 7.41 (d, J=9.8 Hz, 1H), 7.37-7.18 (m, 16H), 6.14 (d, J=2.4 Hz, 1H), 5.67 (d, J=5.4 Hz, 1H), 5.47 (t, J=5.0 Hz, 1H), 5.03-4.96 (m, 2H), 4.95-4.87 (m, 2H), 4.82-4.77 (m, 2H), 4.59-4.53 (m, 1H), 4.49-4.39 (m, 2H), 4.20-4.08 (m, 2H), 3.73-3.62 (m, 1H), 3.04-2.91 (m, 1H), 2.78 (s, 3H), 2.46-2.19 (m, 1H), 1.84-1.74 (m, 2H), 1.69-1.45 (m, 2H), 1.25 (d, J=6.9 Hz, 4H), 1.16 (d, J=7.0 Hz, 3H), 0.93 (t, J=11.8 Hz, 1H), 0.86 (d, J=6.6 Hz, 3H), 0.81 (t, J=6.9 Hz, 6H), 0.74 (dd, J=13.2, 6.7 Hz, 6H), 0.61 (d, J=6.5 Hz, 3H), −0.61 (t, J=12.4 Hz, 1H).

$^{13}$C NMR (101 MHz, DMSO-d6): δ 173.05, 172.44, 172.32, 171.24, 170.94, 169.90, 169.31, 165.80, 159.85, 138.86, 137.61, 136.88, 129.80, 128.60, 128.31, 128.18, 127.76, 127.58, 127.42, 126.44, 125.57, 80.07, 72.34, 68.65, 65.38, 62.49, 58.13, 55.44, 54.98, 54.19, 47.26, 47.05, 31.86, 29.63, 28.77, 28.66, 25.83, 23.15, 19.46, 19.38, 18.94, 18.62, 18.45, 17.03, 16.85.

LC-MS (ESI): $t_R$=8.82 min; m/z=1025.3 [M+H]$^+$, 1007.2 [M+H−H$_2$O]$^+$, 1047.6 [M+Na]$^+$, calcd. for $C_{54}H_{72}N_8O_{12}$: 1024.53.

Ahp4 (21)

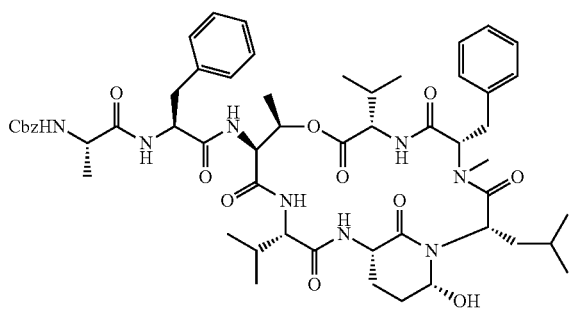

21

Ahp4 (21) was synthesized via the 'general synthesis procedure for Ahp-cyclodepsipeptides'.

Yield: 1.4 mg (1.3 μmol, 0.7%) as a white solid.

$^1$H NMR (700 MHz, DMSO-d6): δ 8.83 (d, J=9.6 Hz, 1H), 8.43 (d, J=4.1 Hz, 1H), 8.33 (d, J=8.2 Hz, 1H), 8.07 (d, J=9.8 Hz, 1H), 7.50 (d, J=9.9 Hz, 1H), 7.41-7.01 (m, 16H), 5.67 (d, J=5.4 Hz, 1H), 5.44 (t, J=5.4 Hz, 1H), 5.17 (qd, J=6.2, 1.9 Hz, 1H), 4.93 (s, 2H), 4.88-4.84 (m, 2H), 4.69 (dd, J=9.7, 3.3 Hz, 1H), 4.59 (dd, J=9.8, 2.0 Hz, 1H), 4.50-4.42 (m, 2H), 4.18-4.11 (m, 1H), 4.09-4.05 (m, 1H), 3.64-3.59 (m, 1H), 3.22 (dd, J=14.4, 4.8 Hz, 1H), 2.92-2.82 (m, 1H), 2.80 (dd, J=14.5, 9.5 Hz, 1H), 2.73 (s, 3H), 2.39-2.28 (m, 1H), 1.81-1.79 (m, 1H), 1.76-1.70 (m, 1H), 1.62-1.57 (m, 1H), 1.50-1.47 (m, 1H), 1.24 (s, 2H), 1.14 (d, J=7.2 Hz, 3H), 1.11 (d, J=6.2 Hz, 3H), 0.84 (d, J=6.7 Hz, 4H), 0.79 (dd, J=13.8, 6.8 Hz, 6H), 0.73 (d, J=6.6 Hz, 3H), 0.70 (d, J=6.8 Hz, 3H), 0.57 (d, J=6.6 Hz, 4H), −0.69 (t, J=12.3 Hz, 1H).

$^{13}$C NMR (176 MHz, DMSO-d6): δ 173.04, 171.33, 171.25, 171.03, 170.90, 170.25, 169.74, 166.36, 155.31, 138.81, 137.98, 136.94, 129.86, 129.16, 128.55, 128.19, 127.98, 127.56, 127.25, 79.98, 72.69, 65.34, 62.43, 58.28, 55.62, 54.93, 54.71, 53.97, 52.61, 49.57, 47.17, 39.53, 37.11, 35.49, 33.27, 31.72, 30.89, 29.58, 28.84, 28.76, 23.41, 23.22, 19.52, 19.45, 19.37, 18.63, 18.40, 16.83, 16.20.

LC-MS (ESI): $t_R$=7.47 min; m/z=1039.2 [M+H]$^+$, 1021.1 [M+H−H$_2$O]$^+$, 1061.5 [M+Na]$^+$, calcd. for $C_{55}H_{74}N_8O_{12}$: 1038.54.

Ahp5 (22)

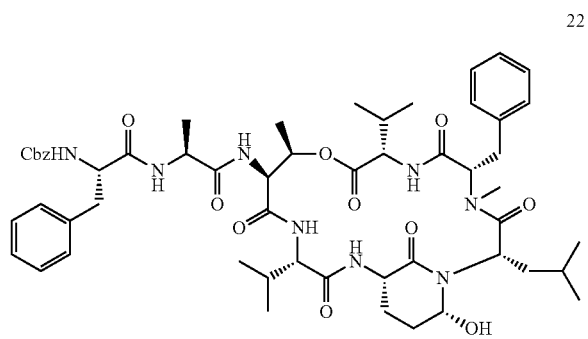 [SMILES: CC(C)C[C@H]1C(=O)N(C)[C@@H](Cc2ccccc2)C(=O)N[C@@H](C(C)C)C(=O)O[C@H](C)[C@H](NC(=O)[C@H](C)NC(=O)[C@H](Cc2ccccc2)NC(=O)OCc2ccccc2)C(=O)N[C@@H](C(C)C)C(=O)N[C@H]2CC[C@@H](O)N1C2=O]

22

Ahp5 (22) was synthesized via the 'general synthesis procedure for Ahp-cyclodepsipeptides'.

Yield: 2.1 mg (2.0 μmol, 1.0%) as a white solid.

$^1$H NMR (700 MHz, DMSO-d6): δ 8.98 (d, J=9.6 Hz, 1H), 8.80 (d, J=7.5 Hz, 1H), 8.49 (d, J=4.1 Hz, 1H), 8.10 (d, J=9.7 Hz, 1H), 7.43-6.89 (m, 17H), 5.68 (d, J=5.4 Hz, 1H), 5.45 (t, J=5.3 Hz, 1H), 5.12-5.09 (m, 1H), 4.96 (dd, J=11.6, 3.0 Hz, 1H), 4.76 (d, J=2.8 Hz, 2H), 4.63 (dd, J=9.8, 1.7 Hz, 1H), 4.58 (q, J=7.3 Hz, 1H), 4.55-4.51 (m, 1H), 4.45 (d, J=9.4 Hz, 2H), 4.08 (dd, J=9.7, 8.0 Hz, 1H), 3.86 (dd, J=14.1, 2.7 Hz, 1H), 3.39 (q, J=7.0 Hz, 2H), 2.96-2.90 (m, 2H), 2.78 (s, 3H), 2.65-2.59 (m, 1H), 2.34-2.30 (m, 1H), 1.81-1.78 (m, 1H), 1.76-1.70 (m, 1H), 1.68-1.62 (m, 1H), 1.58-1.51 (m, 1H), 1.50-1.48 (m, 1H), 1.30 (d, J=7.0 Hz, 3H), 1.10 (t, J=7.0 Hz, 3H), 1.05 (d, J=6.2 Hz, 3H), 0.96-0.90 (m, 1H), 0.87-0.80 (m, 6H), 0.77 (d, J=6.7 Hz, 3H), 0.71 (d, J=6.8 Hz, 3H), 0.63 (d, J=6.7 Hz, 3H), −0.57--0.67 (m, 1H).

$^{13}$C NMR (176 MHz, DMSO-d6): δ 173.52, 173.11, 172.35, 171.77, 171.32, 169.89, 166.82, 156.05, 139.35, 138.42, 137.17, 130.41, 129.51, 129.17, 128.71, 128.46, 127.83, 127.42, 80.51, 73.80, 65.76, 65.38, 62.94, 58.67, 56.32, 55.95, 55.18, 54.00, 47.60, 32.07, 30.13, 29.32, 29.20, 23.95, 23.70, 20.19, 19.89, 19.13, 18.82, 17.22, 16.64, 15.64, 15.54.

LC-MS (ESI): $t_R$=9.40 min; m/z=1039.0 [M+H]$^+$, 1021.0 [M+H−H$_2$O]$^+$, 1061.4 [M+Na]$^+$, calcd. for $C_{55}H_{74}N_8O_{12}$: 1038.54.

Ahp6 (23)

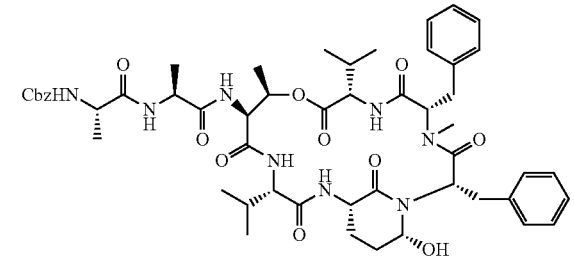

23

Ahp6 (23) was synthesized via the 'general synthesis procedure for Ahp-cyclodepsipeptides'.

Yield: 2.6 mg (2.6 μmol, 1.3%) as a white solid.

$^1$H NMR (700 MHz, DMSO-d6): δ 8.80 (d, J=9.8 Hz, 1H), 8.50 (d, J=3.6 Hz, 1H), 8.43 (d, J=7.4 Hz, 1H), 8.09 (d, J=9.8 Hz, 1H), 7.63 (d, J=9.8 Hz, 1H), 7.36 (d, J=9.1 Hz, 1H), 7.28-7.10 (m, 15H), 5.64 (d, J=5.5 Hz, 1H), 5.42 (t, J=5.3 Hz, 1H), 5.14-5.10 (m, 2H), 5.00 (d, J=12.4 Hz, 1H), 4.96-4.88 (m, 2H), 4.71-4.66 (m, 2H), 4.60 (q, J=7.2 Hz, 1H), 4.29 (d, J=9.2 Hz, 1H), 4.24 (p, J=7.4 Hz, 1H), 3.98 (dd, J=9.7, 7.5 Hz, 1H), 3.86 (d, J=13.7 Hz, 1H), 2.90 (t, J=12.8 Hz, 1H), 2.78 (s, 3H), 2.33-2.27 (m, 1H), 2.21-2.17 (m, 2H), 2.04-1.95 (m, 1H), 1.73-1.71 (m, 1H), 1.67-1.63 (m, 1H), 1.52-1.49 (m, 1H), 1.47-1.45 (m, 1H), 1.26 (d, J=7.1 Hz, 3H), 1.21 (d, J=7.3 Hz, 3H), 1.10 (d, J=6.2 Hz, 3H), 0.81 (d, J=6.9 Hz, 3H), 0.74-0.70 (m, 9H).

LC-MS (ESI): $t_R$=8.58 min; m/z=997.1 [M+H]$^+$, 979.0 [M+H-H$_2$O]$^+$, 1019.5 [M+Na]$^+$, calcd. for C$_{52}$H$_{68}$N$_8$O$_{12}$: 996.50.

Ahp7 (24)

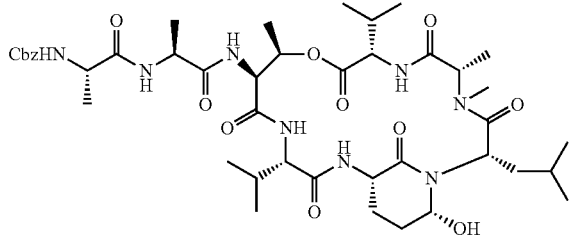

24

Ahp7 (24) was synthesized via the 'general synthesis procedure for Ahp-cyclodepsipeptides'.

Yield: 1.9 mg (2.1 μmol, 1.1%) as a white solid.

$^1$H NMR (400 MHz, DMSO-d6): δ 8.74 (d, J=3.7 Hz, 1H), 8.55 (d, J=9.7 Hz, 1H), 8.40 (d, J=7.4 Hz, 1H), 8.09 (d, J=9.6 Hz, 1H), 7.37-7.28 (m, 6H), 7.25 (d, J=9.2 Hz, 1H), 5.69 (d, J=5.4 Hz, 1H), 5.46 (t, J=5.2 Hz, 1H), 5.10-5.06 (m, 1H), 5.02 (d, J=3.3 Hz, 3H), 4.94-4.87 (m, 1H), 4.61-4.32 (m, 4H), 4.29-3.99 (m, 3H), 2.56 (s, 3H), 1.94-1.74 (m, 2H), 1.70-1.47 (m, 2H), 1.39 (d, J=6.6 Hz, 3H), 1.23 (d, J=5.4 Hz, 3H), 1.20-1.10 (m, 5H), 1.04 (t, J=6.2 Hz, 7H), 0.98 (d, J=6.6 Hz, 3H), 0.91-0.85 (m, 4H), 0.84-0.71 (m, 6H), 0.68 (d, J=6.8 Hz, 3H).

LC-MS (ESI): $t_R$=7.47 min; m/z=887.1 [M+H]$^+$, 869.1 [M+H-H$_2$O]$^+$, 909.5 [M+Na]$^+$, calcd. for C$_{43}$H$_{66}$N$_8$O$_{12}$: 886.48.

Ahp8 (25)

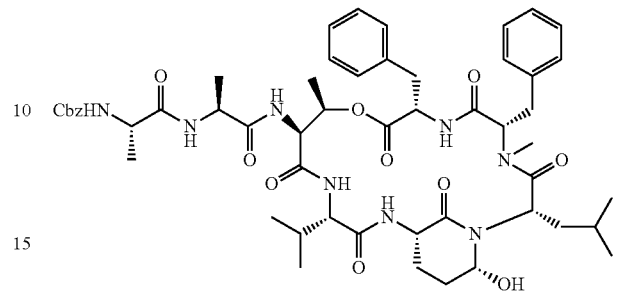

25

Ahp8 (25) was synthesized via the 'general synthesis procedure for Ahp-cyclodepsipeptides'.

Yield: 13.2 mg (13.1 μmol, 6.6%) as a white solid.

$^1$H NMR (700 MHz, DMSO-d6): δ 9.23 (d, J=9.5 Hz, 1H), 8.59 (d, J=3.8 Hz, 1H), 8.46 (d, J=7.4 Hz, 1H), 8.13 (d, J=9.8 Hz, 1H), 7.47 (d, J=9.8 Hz, 1H), 7.38-7.04 (m, 16H), 5.74 (d, J=5.5 Hz, 1H), 5.61 (t, J=5.4 Hz, 1H), 5.16-5. (m, 1H), 4.93-4.86 (m, 3H), 4.71 (dd, J=11.5, 3.2 Hz, 1H), 4.65 (dd, J=9.8, 2.1 Hz, 1H), 4.56-4.50 (m, 3H), 4.27-4.20 (m, 1H), 4.17-4.13 (m, 1H), 3.71-3.65 (m, 1H), 2.67-2.60 (m, 1H), 2.51 (s, 3H) 1.90-1.86 (m, 1H), 1.82-1.72 (m, 1H), 1.66-1.62 (m, 2H), 1.40 (d, J=3.9 Hz, 3H), 1.24 (d, J=6.7 Hz, 3H), 1.21 (d, J=7.3 Hz, 2H), 1.11 (d, J=6.1 Hz, 3H), 0.93 (t, J=13.1 Hz, 1H), 0.85 (d, J=6.7 Hz, 3H), 0.78-0.76 (m, 8H), 0.61 (d, J=6.7 Hz, 3H), −0.53 (dd, J=18.5, 6.5 Hz, 1H).

$^{13}$C NMR (176 MHz, DMSO-d6): δ 173.24, 172.38, 171.91, 171.77, 171.05, 170.51, 170.33, 169.51, 166.44, 155.35, 138.97, 137.71, 136.90, 129.70, 128.96, 128.55, 128.21, 128.07, 127.44, 127.12, 118.08, 80.26, 73.55, 65.31, 62.48, 59.75, 58.37, 54.92, 54.71, 53.70, 51.85, 49.32, 47.26, 47.02, 37.74, 36.65, 32.49, 31.69, 31.28, 28.85, 28.24, 26.34, 23.50, 23.29, 20.77, 19.68, 19.52, 18.71, 18.25, 15.99, 15.45, 14.09, 1.16.

LC-MS (ESI): $t_R$=8.76 min; m/z=1011.2 [M+H]$^+$, 993.1 [M+H-H$_2$O]$^+$, 1033.1 [M+Na]$^+$, calcd. for C$_{53}$H$_{70}$N$_8$O$_{12}$: 1010.51.

Ahp9 (26)

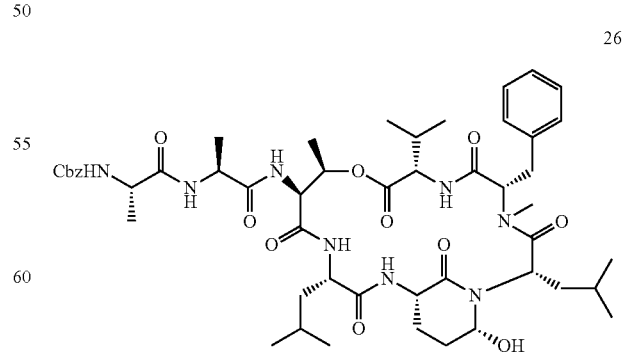

26

Ahp9 (26) was synthesized via the 'general synthesis procedure for Ahp-cyclodepsipeptides'.

Yield: 11.8 mg (12.1 μmol, 6.1%) as a white solid.

¹H NMR (400 MHz, DMSO-d6): δ 8.84 (d, J=9.7 Hz, 1H), 8.54 (d, J=4.1 Hz, 1H), 8.48 (d, J=7.5 Hz, 1H), 8.11 (d, J=9.6 Hz, 1H), 7.41 (d, J=9.9 Hz, 1H), 7.38-7.03 (m, 11H), 5.70-5.48 (m, 1H), 5.45-5.36 (m, 1H), 5.09 (dt, J=7.9, 5.6 Hz, 1H), 4.90 (s, 3H), 4.67 (dd, J=9.7, 3.2 Hz, 1H), 4.58-4.48 (m, 3H), 4.40-4.21 (m, 3H), 3.84-3.72 (m, 1H), 2.94-2.87 (m, 1H), 2.75 (s, 3H), 2.45-2.24 (m, 2H), 1.88-1.78 (m, 1H), 1.65-1.55 (m, 1H), 1.49 (q, J=5.8, 3.4 Hz, 2H), 1.45-1.32 (m, 2H), 1.31-1.09 (m, 8H), 1.05 (d, J=6.1 Hz, 3H), 0.99-0.73 (m, 12H), 0.69 (d, J=6.8 Hz, 3H), 0.58 (d, J=6.5 Hz, 3H), −0.67 (t, J=12.4 Hz, 1H).

¹³C NMR (101 MHz, DMSO-d6): δ 173.33, 173.12, 171.96, 171.18, 170.49, 169.48, 166.25, 155.37, 138.91, 136.85, 129.92, 128.67, 128.05, 127.43, 127.10, 126.39, 79.77, 73.18, 65.35, 62.35, 58.35, 55.56, 53.60, 49.27, 47.66, 47.03, 46.94, 38.86, 37.05, 30.90, 29.58, 28.72, 23.95, 23.32, 23.25, 23.17, 21.16, 19.54, 19.45, 19.17, 16.70, 15.95, 15.27.

LC-MS (ESI): $t_R$=8.73 min; m/z=977.1 [M+H]⁺, 959.1 [M+H−H₂O]⁺, 994.0 [M+Na]⁺, calcd. for $C_{50}H_{72}N_8O_{12}$: 976.53.

Ahp10 (27)

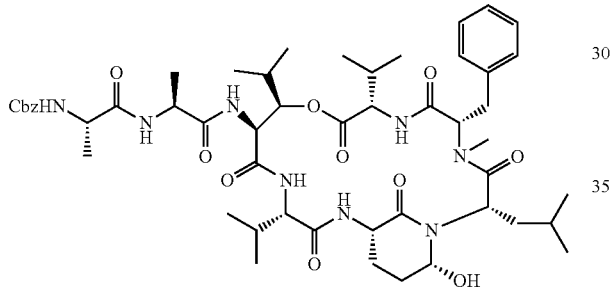

Ahp10 (27) was synthesized via the 'general synthesis procedure for Ahp-cyclodepsipeptides'.

Yield: 12.5 mg (12.6 μmol, 6.3%) as a white solid.

¹H NMR (400 MHz, DMSO-d6): δ 8.33 (d, J=9.6 Hz, 1H), 7.99-7.96 (m, 2H), 7.45 (d, J=7.7 Hz, 1H), 7.42-7.09 (m, 12H), 5.93 (d, J=3.2 Hz, 1H), 5.15-5.06 (m, 2H), 5.02 (s, 2H), 4.93 (dd, J=9.7, 3.0 Hz, 1H), 4.87 (d, J=3.2 Hz, 1H), 4.81-4.74 (m, 1H), 4.54 (dd, J=11.1, 4.0 Hz, 1H), 4.50-4.43 (m, 1H), 4.43-4.35 (m, 1H), 4.30 (dd, J=9.6, 4.0 Hz, 1H), 4.07 (p, J=7.2 Hz, 1H), 3.22 (dd, J=14.3, 2.9 Hz, 1H), 2.82 (dd, J=14.1, 11.6 Hz, 1H), 2.75 (s, 3H), 2.69-2.55 (m, 1H), 2.45-2.31 (m, 1H), 2.30-2.16 (m, 1H), 2.01-1.91 (m, 1H), 1.84-1.64 (m, 3H), 1.58-1.51 (m, 1H), 1.20 (d, J=7.0 Hz, 6H), 0.91 (dd, J=6.9, 4.3 Hz, 6H), 0.86 (d, J=6.5 Hz, 3H), 0.81 (d, J=6.9 Hz, 3H), 0.77 (d, J=6.9 Hz, 3H), 0.68 (dd, J=10.2, 6.7 Hz, 7H), 0.43 (d, J=6.5 Hz, 3H), 0.27-0.21 (m, 1H).

¹³C NMR (101 MHz, DMSO-d6): δ 172.62, 172.15, 171.64, 170.38, 169.91, 169.84, 169.42, 169.15, 158.75, 137.53, 137.02, 129.23, 128.57, 128.32, 127.73, 127.64, 126.42, 73.37, 67.26, 65.29, 60.51, 56.95, 55.61, 52.46, 49.82, 48.57, 47.65, 47.56, 33.88, 30.81, 30.62, 27.76, 23.79, 23.53, 22.24, 19.65, 19.21, 19.05, 18.44, 18.14, 18.04, 16.16.

LC-MS (ESI): $t_R$=8.67 min; m/z=991.0 [M+H]⁺, 973.2 [M+H−H₂O]⁺, 1013.5 [M+Na]⁺, calcd. for $O_{51}H_{74}N_8O_{12}$: 990.54.

Ahp11

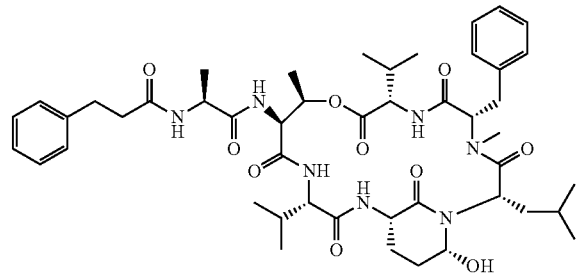 [SMILES: CC(C)C[C@H]1C(=O)N(C)[C@@H](Cc2ccccc2)C(=O)N[C@@H](C(C)C)C(=O)O[C@H](C)[C@H](NC(=O)[C@H](C)NC(=O)CCc2ccccc2)C(=O)N[C@@H](C(C)C)C(=O)N[C@H]2CC[C@@H](O)N1C2=O]

Ahp11 was synthesized via the 'general synthesis procedure for Ahp-cyclodepsipeptides'.

Yield: 3.7 mg (4.2 μmol, 2.1%) as a white solid.

¹H NMR (400 MHz, DMSO-d6): δ 8.73 (d, J=9.6 Hz, 1H), 8.41 (d, J=3.9 Hz, 1H), 8.27 (d, J=7.6 Hz, 1H), 8.00 (d, J=9.6 Hz, 1H), 7.44 (d, J=9.4 Hz, 1H), 7.32-7.22 (m, 10H), 5.44 (d, J=4.6 Hz, 1H), 5.15 (dd, J=6.3, 2.4 Hz, 1H), 4.84 (dd, J=11.5, 3.1 Hz, 1H), 4.77-4.69 (m, 1H), 4.63 (dd, J=9.6, 3.5 Hz, 1H), 4.60-4.53 (m, 1H), 4.50 (dd, J=14.0, 6.7 Hz, 1H), 4.43 (d, J=9.0 Hz, 1H), 4.06 (dd, J=9.6, 7.8 Hz, 1H), 3.59-3.46 (m, 1H), 2.96 (dd, J=14.1, 11.5 Hz, 1H), 2.85 (m, 2H), 2.74 (s, 4H), 2.46-2.24 (m, 2H), 1.86-1.68 (m, 2H), 1.68-1.45 (m, 2H), 1.21 (dt, J=7.4, 3.7 Hz, 5H), 1.08 (d, J=6.2 Hz, 3H), 0.86 (d, J=6.9 Hz, 1H), 0.78 (m, 12H), 0.70 (d, J=6.8 Hz, 2H), 0.66 (d, J=6.6 Hz, 1H), 0.61 (d, J=6.6 Hz, 3H), 0.43 (d, J=6.5 Hz, 1H), −0.60 (t, J=12.3 Hz, 1H).

LC-MS (ESI): $t_R$=8.56 min; m/z=890.25 [M+H]⁺, 872.23 [M+H−H₂O]⁺,±912.67 [M+Na]⁺, calcd. for $C_{51}H_{74}N_8O_{12}$: 889.49.

Ahp12

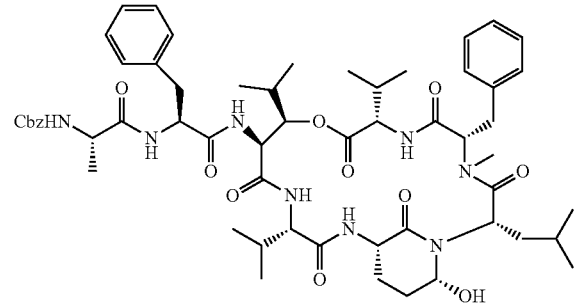 [SMILES: CC(C)C[C@H]1C(=O)N(C)[C@@H](Cc2ccccc2)C(=O)N[C@@H](C(C)C)C(=O)O[C@H](C(C)C)[C@H](NC(=O)[C@H](Cc2ccccc2)NC(=O)[C@H](C)NC(=O)OCc2ccccc2)C(=O)N[C@@H](C(C)C)C(=O)N[C@H]2CC[C@@H](O)N1C2=O]

Ahp12 was synthesized via the 'general synthesis procedure for Ahp-cyclodepsipeptides'.

Yield: 1.0 mg (0.9 μmol, 0.5%) as a white solid.

¹H NMR (700 MHz, DMSO-d6): δ 9.05 (d, J=9.6 Hz, 1H), 8.45-8.41 (m, 1H), 8.24 (t, J=8.5 Hz, 2H), 7.59 (d, J=10.0 Hz, 1H), 7.36 (t, J=6.3 Hz, 1H), 7.34-7.18 (m, 15H), 5.65-5.61 (m, 1H), 5.48 (t, J=5.3 Hz, 1H), 5.11 (d, J=10.1 Hz, 1H), 4.94 (d, J=9.5 Hz, 2H), 4.79 (m, 3H), 4.60 (m, 1H), 4.56-4.52 (m, 1H), 4.41 (d, J=9.1 Hz, 1H), 4.12 (q, J=7.8 Hz, 1H), 4.08-4.01 (m, 2H), 3.64-3.56 (m, 1H), 2.87 (m, 1H), 2.74 (s, 5H), 2.12 (m, 1H), 1.80-1.72 (m, 2H), 1.56 (m, 2H), 1.48 (d, J=12.3, 6.8 Hz, 1H), 1.14 (d, J=7.2 Hz, 3H), 0.97 (d, J=6.9 Hz, 2H), 0.83 (t, J=7.1 Hz, 6H), 0.77 (d, J=6.6 Hz, 12H), 0.68 (d, J=6.6 Hz, 3H), 0.54 (d, J=6.5 Hz, 3H), −0.69 (t, J=12.4 Hz, 1H).

LC-MS (ESI): $t_R$=9.47 min; m/z=1067.30 [M+H]$^+$, 1049.19 [M+H–H$_2$O]$^+$, 1089.67 [M+Na]$^+$, calcd. for C$_{57}$H$_{78}$N$_8$O$_{12}$: 1066.57.

Ahp13

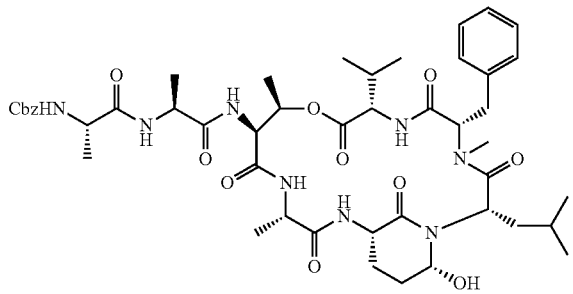 [SMILES: CC(C)C[C@H]1C(=O)N(C)[C@@H](Cc2ccccc2)C(=O)N[C@@H](C(C)C)C(=O)O[C@H](C)[C@H](NC(=O)[C@H](C)NC(=O)[C@H](C)NC(=O)OCc2ccccc2)C(=O)N[C@@H](C)C(=O)N[C@H]2CC[C@@H](O)N1C2=O]

Ahp13 was synthesized via the 'general synthesis procedure for Ahp-cyclodepsipeptides'.

Yield: 1.2 mg (1.3 μmol, 0.6%) as a white solid.

$^1$H NMR (400 MHz, DMSO-d6): δ 8.81 (d, J=9.6 Hz, 1H), 8.50 (d, J=7.6 Hz, 1H), 8.44 (d, J=4.1 Hz, 1H), 8.24 (d, J=9.4 Hz, 1H), 7.40-7.10 (m, 12H), 5.60 (d, J=5.4 Hz, 1H), 5.44-5.38 (m, 1H), 5.13 (dt, J=6.3, 3.6 Hz, 1H), 4.90 (d, J=2.2 Hz, 2H), 4.65 (dd, J=9.6, 3.4 Hz, 1H), 4.49 (dd, J=8.6, 6.0 Hz, 2H), 4.41 (dd, J=9.1, 5.9 Hz, 2H), 4.32-4.22 (m, 1H), 4.09 (q, J=5.4 Hz, 1H), 3.76 (d, J=13.4 Hz, 1H), 3.17 (d, J=4.8 Hz, 1H), 2.89 (dd, J=13.8, 11.2 Hz, 1H), 2.74 (s, 3H), 1.90-1.82 (m, 1H), 1.62 (s, 1H), 1.50 (dt, J=10.6, 4.8 Hz, 2H), 1.22 (dd, J=14.6, 7.0 Hz, 8H), 1.06 (dd, J=19.5, 6.5 Hz, 6H), 0.92 (t, J=12.9 Hz, 1H), 0.81 (dd, J=8.7, 6.7 Hz, 6H), 0.70 (d, J=6.8 Hz, 3H), 0.60 (d, J=6.6 Hz, 3H).

LC-MS (ESI): $t_R$=7.98 min; m/z=935.23 [M+H]$^+$, 917.28 [M+H–H$_2$O]$^+$, 957.61 [M+Na]$^+$, calcd. for C$_{47}$H$_{66}$N$_8$O$_{12}$: 934.48.

Ahp14

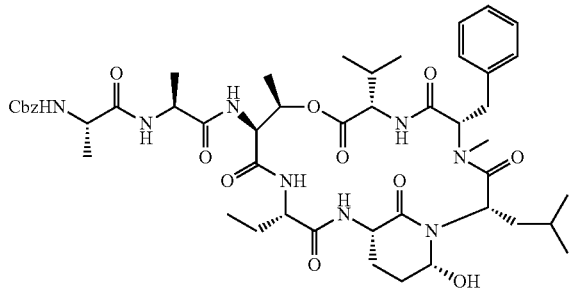 [SMILES: CC[C@@H]1NC(=O)[C@@H](NC(=O)[C@H](C)NC(=O)[C@H](C)NC(=O)OCc2ccccc2)[C@@H](C)OC(=O)[C@H](C(C)C)NC(=O)[C@H](Cc2ccccc2)N(C)C(=O)[C@H](CC(C)C)N2C(=O)[C@H](CC[C@H]2O)NC1=O]

Ahp14 was synthesized via the 'general synthesis procedure for Ahp-cyclodepsipeptides'.

Yield: 1.2 mg (1.3 μmol, 1.3%) as a white solid.

$^1$H NMR (400 MHz, DMSO-d6): δ 8.83 (d, J=9.6 Hz, 1H), 8.50 (d, J=7.5 Hz, 1H), 8.44 (d, J=4.0 Hz, 1H), 8.14 (d, J=9.6 Hz, 1H), 7.36-7.09 (m, 12H), 5.42 (d, J=4.5 Hz, 1H), 5.11 (m, 1H), 4.91 (d, J=6.1 Hz, 3H), 4.66 (dd, J=9.7, 3.3 Hz, 1H), 4.58-4.47 (m, 3H), 4.42 (d, J=9.0 Hz, 1H), 4.32-4.19 (m, 2H), 3.85-3.73 (m, 1H), 2.89 (dd, J=13.9, 11.4 Hz, 1H), 2.75 (s, 3H), 1.82 (dd, J=12.3, 6.2 Hz, 1H), 1.69-1.58 (m, 1H), 1.57-1.47 (m, 3H), 1.36 (m, 1H), 1.28-1.17 (m, 9H), 1.04 (d, J=6.2 Hz, 3H), 0.94 (m, 1H), 0.84-0.77 (m, 9H), 0.70 (d, J=6.8 Hz, 3H), 0.61 (d, J=6.5 Hz, 3H), –0.62 (t, J=12.4 Hz, 1H).

LC-MS (ESI): $t_R$=8.13 min; m/z=949.65 [M+H]$^+$, 931.18 [M+H–H$_2$O]$^+$, 971.72 [M+Na]$^+$, calcd. for C$_{48}$H$_{68}$N$_8$O$_{12}$: 948.50.

Ahp15

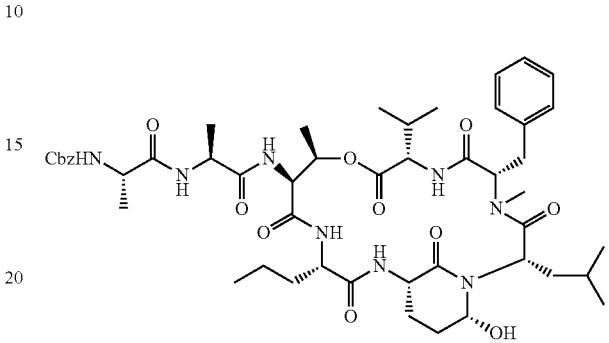

Ahp15 was synthesized via the 'general synthesis procedure for Ahp-cyclodepsipeptides'.

Yield: 1.0 mg (1.0 μmol, 1.0%) as a white solid.

$^1$H NMR (400 MHz, DMSO-d6): δ 8.84 (d, J=9.7 Hz, 1H), 8.48 (t, J=5.5 Hz, 2H), 8.12 (d, J=9.6 Hz, 1H), 7.39-7.03 (m, 13H), 5.42 (d, J=4.3 Hz, 1H), 5.10 (m, 1H), 4.90 (s, 3H), 4.66 (dd, J=9.7, 3.3 Hz, 1H), 4.59-4.44 (m, 3H), 4.41-4.21 (m, 3H), 3.79 (dd, J=14.1, 2.6 Hz, 1H), 2.90 (dd, J=13.9, 11.5 Hz, 1H), 2.74 (s, 3H), 1.88-1.78 (m, 1H), 1.62 (m, 1H), 1.50 (dt, J=11.1, 4.8 Hz, 2H), 1.39 (m, 2H), 1.28-1.18 (m, 9H), 1.05 (d, J=6.2 Hz, 3H), 0.99-0.87 (m, 1H), 0.85-0.76 (m, 9H), 0.69 (d, J=6.8 Hz, 3H), 0.60 (d, J=6.6 Hz, 4H), –0.64 (t, J=12.4 Hz, 1H).

LC-MS (ESI): $t_R$=8.31 min; m/z=963.18 [M+H]$^+$, 945.36 [M+H–H$_2$O]$^+$, 985.64 [M+Na]$^+$, calcd. for C$_{49}$H$_{70}$N$_8$O$_{12}$: 962.51.

Ahp16

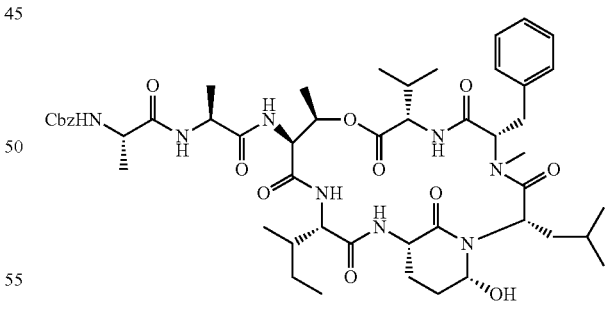

Ahp16 was synthesized via the 'general synthesis procedure for Ahp-cyclodepsipeptides'.

Yield: 2.3 mg (2.4 μmol, 1.2%) as a white solid.

$^1$H NMR (400 MHz, DMSO-d6): δ 8.90 (d, J=9.6 Hz, 1H), 8.50 (d, J=7.4 Hz, 1H), 8.43 (d, J=4.2 Hz, 1H), 8.04 (dd, J=8.6, 2.5 Hz, 1H), 7.42-7.01 (m, 12H), 5.44 (d, J=5.0 Hz, 1H), 5.13-5.04 (m, 1H), 4.91 (d, J=5.4 Hz, 3H), 4.67 (dd, J=9.6, 3.2 Hz, 1H), 4.59-4.42 (m, 4H), 4.34-4.23 (m, 1H), 4.11 (t, J=9.4 Hz, 1H), 3.84-3.73 (m, 1H), 2.90 (dd, J=13.9, 11.4 Hz, 1H), 2.75 (s, 3H), 2.33 (m, 1H), 1.79 (dd,

J=12.4, 6.8 Hz, 1H), 1.55 (m, 4H), 1.34 (dqd, J=14.7, 7.3, 3.0 Hz, 1H), 1.22 (dd, J=18.4, 7.1 Hz, 9H), 1.04 (d, J=6.1 Hz, 3H), 1.01-0.86 (m, 1H), 0.78 (dt, J=22.8, 6.8 Hz, 12H), 0.69 (d, J=6.8 Hz, 3H), 0.60 (d, J=6.6 Hz, 3H), −0.62 (t, J=12.4 Hz, 1H).

LC-MS (ESI): $t_R$=8.63 min; m/z=977.20 [M+H]$^+$, 959.25 [M+H−H$_2$O]$^+$, 999.61 [M+Na]$^+$, calcd. for C$_{50}$H$_{72}$N$_8$O$_{12}$: 976.53.

Ahp17

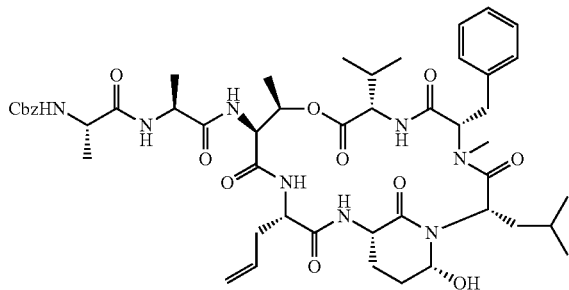 [SMILES: C=CC[C@@H]1NC(=O)[C@@H](NC(=O)[C@H](C)NC(=O)[C@H](C)NC(=O)OCc2ccccc2)[C@@H](C)OC(=O)[C@H](C(C)C)NC(=O)[C@H](Cc2ccccc2)N(C)C(=O)[C@H](CC(C)C)N2C(=O)[C@H](CC[C@H]2O)NC1=O]

Ahp17 was synthesized via the 'general synthesis procedure for Ahp-cyclodepsipeptides'.

Yield: 1.1 mg (1.1 μmol, 1.1%) as a white solid.

$^1$H NMR (400 MHz, DMSO-d6): δ 8.83 (d, J=9.6 Hz, 1H), 8.52 (d, J=7.3 Hz, 1H), 8.45 (d, J=4.2 Hz, 1H), 8.22 (d, J=9.5 Hz, 1H), 7.44-7.01 (m, 13H), 5.62 (d, J=5.5 Hz, 1H), 5.42 (d, J=5.2 Hz, 1H), 5.16-5.11 (m, 1H), 5.07 (d, J=1.9 Hz, 1H), 5.04-4.99 (m, 2H), 4.90 (d, J=6.0 Hz, 3H), 4.66 (dd, J=9.7, 3.3 Hz, 1H), 4.53-4.47 (m, 3H), 4.38 (dd, J=12.1, 7.9 Hz, 2H), 4.32-4.26 (m, 1H), 3.79 (d, J=13.1 Hz, 1H), 2.89 (dd, J=13.8, 11.3 Hz, 1H), 2.74 (s, 3H), 2.40-2.07 (m, 3H), 1.86-1.80 (m, 1H), 1.62 (s, 1H), 1.54-1.44 (m, 3H), 1.20 (d, J=7.3 Hz, 4H), 1.07-1.01 (m, 4H), 0.90-0.82 (m, 2H), 0.80 (t, J=5.9 Hz, 7H), 0.69 (d, J=6.8 Hz, 3H), 0.60 (d, J=6.5 Hz, 3H), −0.63 (t, J=12.5 Hz, 1H).

LC-MS (ESI): $t_R$=8.31 min; m/z=961.32 [M+H]$^+$, 943.30 [M+H−H$_2$O]$^+$, 983.70 [M+Na]$^+$, calcd. for C$_{49}$H$_{68}$N$_8$O$_{12}$: 960.50.

Ahp18

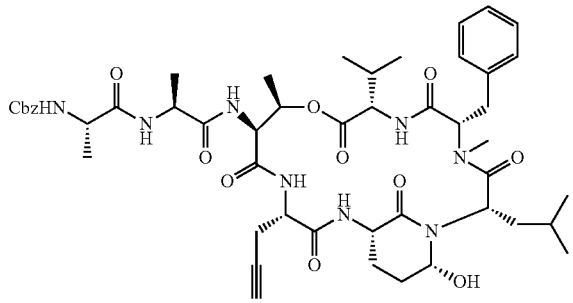 [SMILES: C#CC[C@@H]1NC(=O)[C@@H](NC(=O)[C@H](C)NC(=O)[C@H](C)NC(=O)OCc2ccccc2)[C@@H](C)OC(=O)[C@H](C(C)C)NC(=O)[C@H](Cc2ccccc2)N(C)C(=O)[C@H](CC(C)C)N2C(=O)[C@H](CC[C@H]2O)NC1=O]

Ahp18 was synthesized via the 'general synthesis procedure for Ahp-cyclodepsipeptides'.

Yield: 2.4 mg (2.5 μmol, 2.5%) as a white solid.

LC-MS (ESI): $t_R$=8.23 min; m/z=959.30 [M+H]$^+$, 941.21 [M+H−H$_2$O]$^+$, 981.69 [M+Na]$^+$, calcd. for C$_{49}$H$_{66}$N$_8$O$_{12}$: 958.48.

Ahp19

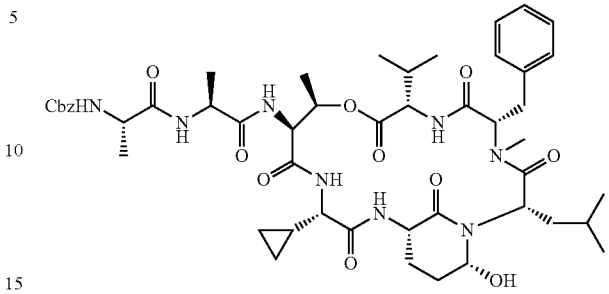

Ahp19 was synthesized via the 'general synthesis procedure for Ahp-cyclodepsipeptides'.

Yield: 2.0 mg (2.1 μmol, 2.1%) as a white solid.

$^1$H NMR (400 MHz, DMSO-d6): δ 8.80 (d, J=9.6 Hz, 1H), 8.49 (d, J=7.6 Hz, 1H), 8.45 (d, J=4.0 Hz, 1H), 8.26 (d, J=9.6 Hz, 1H), 7.41-7.02 (m, 12H), 5.69 (d, J=5.6 Hz, 1H), 5.41 (t, J=5.3 Hz, 1H), 5.13-5.05 (m, 1H), 4.92-4.82 (m, 3H), 4.64 (dd, J=9.7, 3.3 Hz, 1H), 4.61-4.42 (m, 3H), 4.40 (d, J=9.1 Hz, 1H), 4.32-4.21 (m, 1H), 3.95 (m, 1H), 3.79 (d, J=13.9 Hz, 1H), 2.89 (dd, J=14.0, 11.4 Hz, 1H), 2.73 (s, 4H), 2.44-2.22 (m, 1H), 1.78 (dd, J=12.4, 6.4 Hz, 1H), 1.66-1.44 (m, 2H), 1.20 (d, J=7.2 Hz, 5H), 1.04 (d, J=6.1 Hz, 3H), 0.99-0.82 (m, 2H), 0.78 (dd, J=6.8, 3.9 Hz, 7H), 0.68 (d, J=6.8 Hz, 3H), 0.60 (d, J=6.6 Hz, 4H), 0.45-0.29 (m, 3H), 0.13 (m, 1H), −0.63 (t, J=12.4 Hz, 1H).

LC-MS (ESI): $t_R$=8.14 min; m/z=961.31 [M+H]$^+$, 943.27 [M+H−H$_2$O]$^+$, 983.70 [M+Na]$^+$, calcd. for C$_{49}$H$_{66}$N$_8$O$_{12}$: 960.50.

Ahp20

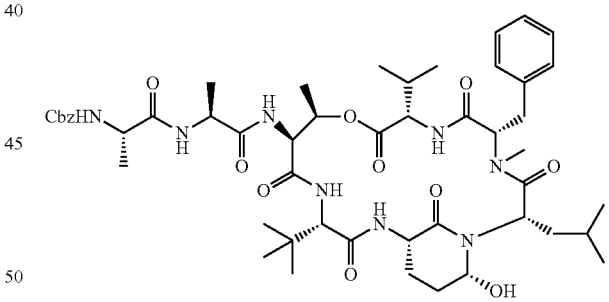

Ahp20 was synthesized via the 'general synthesis procedure for Ahp-cyclodepsipeptides'.

Yield: 1.4 mg (1.4 μmol, 1.4%) as a white solid.

$^1$H NMR (400 MHz, DMSO-d6): δ 8.89 (d, J=9.6 Hz, 1H), 8.53-8.45 (m, 2H), 7.94 (d, J=9.9 Hz, 1H), 7.50-7.44 (m, 1H), 7.41-7.05 (m, 11H), 5.66 (s, 1H), 5.46 (s, 1H), 5.12 (d, J=6.6 Hz, 1H), 5.03 (s, 1H), 4.89 (d, J=14.1 Hz, 3H), 4.66 (dd, J=9.7, 3.2 Hz, 1H), 4.60 (d, J=9.9 Hz, 1H), 4.57-4.48 (m, 2H), 4.28 (q, J=8.4, 7.6 Hz, 1H), 4.19-4.14 (m, 1H), 3.78 (d, J=13.6 Hz, 1H), 2.96-2.84 (m, 1H), 2.75 (d, J=1.4 Hz, 3H), 2.36-2.24 (m, 1H), 1.76 (dd, J=12.1, 7.1 Hz, 1H), 1.68 (d, J=26.3 Hz, 2H), 1.51 (m, 3H), 1.21 (d, J=7.6 Hz, 4H), 1.06 (d, J=6.1 Hz, 3H), 0.85 (s, 11H), 0.80 (dd, J=6.8, 2.7 Hz, 6H), 0.69 (d, J=6.6 Hz, 3H), 0.62 (d, J=6.6 Hz, 3H), −0.60 (t, J=12.4 Hz, 1H).

LC-MS (ESI): $t_R$=8.55 min; m/z=977.43 [M+H]$^+$, 959.33 [M+H–H$_2$O]$^+$, 999.78 [M+Na]$^+$, calcd. for C$_{50}$H$_{72}$N$_8$O$_{12}$: 976.53.

Ahp21

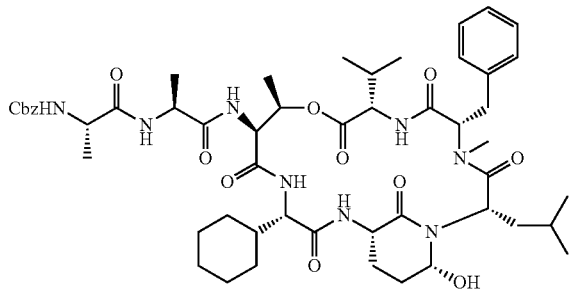 [SMILES: CC(C)C[C@H]1C(=O)N(C)[C@@H](Cc2ccccc2)C(=O)N[C@@H](C(C)C)C(=O)O[C@H](C)[C@H](NC(=O)[C@H](C)NC(=O)[C@H](C)NC(=O)OCc2ccccc2)C(=O)N[C@@H](C2CCCCC2)C(=O)N[C@H]2CC[C@@H](O)N1C2=O]

Ahp21 was synthesized via the 'general synthesis procedure for Ahp-cyclodepsipeptides'.

Yield: 2.9 mg (2.9 μmol, 2.9%) as a white solid.

$^1$H NMR (400 MHz, DMSO-d6): δ 8.86 (d, J=9.6 Hz, 1H), 8.51 (d, J=7.5 Hz, 1H), 8.40 (d, J=4.1 Hz, 1H), 7.99 (d, J=9.7 Hz, 1H), 7.38-7.02 (m, 12H), 5.65 (d, J=5.3 Hz, 1H), 5.42 (t, J=5.2 Hz, 1H), 5.10 (m, 1H), 4.90 (s, 3H), 4.66 (dd, J=9.7, 3.1 Hz, 1H), 4.60-4.42 (m, 5H), 4.34-4.21 (m, 1H), 4.09 (t, J=9.2 Hz, 1H), 3.86-3.74 (m, 1H), 2.95-2.83 (m, 1H), 2.74 (s, 3H), 2.41-2.26 (m, 1H), 1.80 (dd, J=12.4, 6.7 Hz, 2H), 1.56-1.38 (m, 2H), 1.25-1.17 (m, 13H), 1.05 (t, J=7.6 Hz, 5H), 0.97-0.85 (m, 2H), 0.80 (t, J=7.2 Hz, 6H), 0.69 (d, J=6.9 Hz, 3H), 0.62 (d, J=6.6 Hz, 4H), –0.61 (t, J=12.4 Hz, 1H).

LC-MS (ESI): $t_R$=8.93 min; m/z=1003.33 [M+H]$^+$, 985.51 [M+H–H$_2$O]$^+$, 1025.81 [M+Na]$^+$, calcd. for C$_{52}$H$_{74}$N$_8$O$_{12}$: 1002.54.

Ahp22

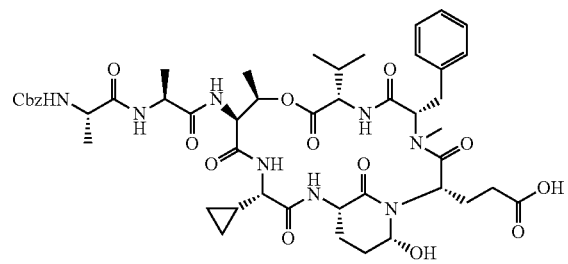 [SMILES: CC(C)[C@@H]1NC(=O)[C@H](Cc2ccccc2)N(C)C(=O)[C@H](CCC(=O)O)N2C(=O)[C@H](CC[C@H]2O)NC(=O)[C@H](C2CC2)NC(=O)[C@@H](NC(=O)[C@H](C)NC(=O)[C@H](C)NC(=O)OCc2ccccc2)[C@@H](C)OC1=O]

Ahp22 was synthesized via the 'general synthesis procedure for Ahp-cyclodepsipeptides'.

Yield: 1.8 mg (1.8 μmol, 1.8%) as a white solid.

$^1$H NMR (400 MHz, DMSO-d6): δ 8.29 (d, J=8.9 Hz, 1H), 7.81 (d, J=7.4 Hz, 1H), 7.63 (d, J=9.2 Hz, 1H), 7.24 (t, J=9.2 Hz, 2H), 7.16-6.92 (m, 11H), 5.79 (d, J=3.2 Hz, 1H), 5.25 (dt, J=7.4, 6.0 Hz, 1H), 4.79 (s, 2H), 4.64 (dt, J=6.5, 3.0 Hz, 2H), 4.48 (dd, J=9.6, 4.5 Hz, 1H), 4.36 (dd, J=9.2, 1.3 Hz, 1H), 4.27-4.16 (m, 3H), 3.85 (m, 1H), 3.70 (t, J=8.3 Hz, 1H), 2.98 (dd, J=14.2, 2.9 Hz, 1H), 2.58 (dd, J=14.0, 11.6 Hz, 1H), 2.50 (s, 3H), 1.90-1.81 (m, 1H), 1.63-1.47 (m, 2H), 1.46-1.32 (m, 1H), 1.23 (dt, J=8.6, 6.1 Hz, 2H), 0.98 (dt, J=13.8, 7.5 Hz, 1H), 0.63 (d, J=6.9 Hz, 3H), 0.52-0.47 (m, 4H), 0.32 (m, 1H), 0.11 (m, 1H), 0.01 (m, 1H), –0.09 (m, 1H).

LC-MS (ESI): $t_R$=7.05 min; m/z=977.27 [M+H]$^+$, 959.28 [M+H–H$_2$O]$^+$, 999.60 [M+Na]$^+$, calcd. for C$_{48}$H$_{64}$N$_8$O$_{14}$: 976.45.

Ahp23

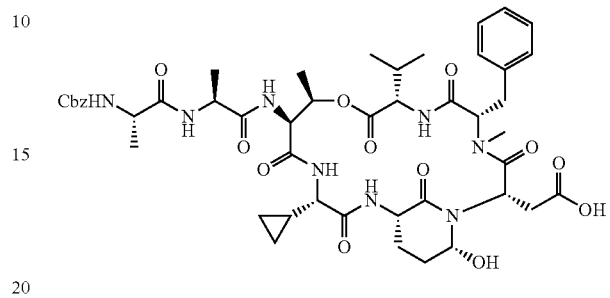

Ahp23 was synthesized via the 'general synthesis procedure for Ahp-cyclodepsipeptides'.

Yield: 0.3 mg (0.3 μmol, 0.3%) as a white solid.

LC-MS (ESI): $t_R$=7.05 min; m/z=963.00 [M+H]$^+$, 945.31 [M+H–H$_2$O]$^+$, 985.61 [M+Na]$^+$, calcd. for C$_{47}$H$_{62}$N$_8$O$_{14}$: 962.44.

Ahp24

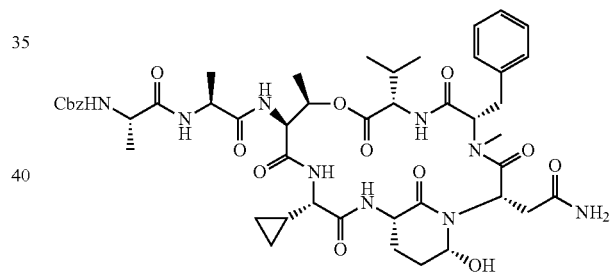

Ahp24 was synthesized via the 'general synthesis procedure for Ahp-cyclodepsipeptides'.

Yield: 2.3 mg (2.4 μmol, 2.4%) as a white solid.

$^1$H NMR (400 MHz, DMSO-d6): δ 8.27 (d, J=8.9 Hz, 1H), 7.81 (d, J=7.3 Hz, 1H), 7.69 (d, J=9.2 Hz, 1H), 7.24 (d, J=7.7 Hz, 1H), 7.17-6.93 (m, 12H), 6.72 (d, J=2.5 Hz, 1H), 6.51 (d, J=2.5 Hz, 1H), 5.68 (d, J=3.2 Hz, 1H), 5.26 (dt, J=7.5, 5.9 Hz, 1H), 4.98 (m, 2H), 4.80 (s, 2H), 4.76 (t, J=3.1 Hz, 1H), 4.48 (dd, J=9.5, 4.3 Hz, 1H), 4.37 (dd, J=9.2, 1.4 Hz, 1H), 4.23 (p, J=7.1 Hz, 1H), 4.06 (ddd, J=12.3, 9.0, 6.6 Hz, 1H), 3.86 (p, J=7.2 Hz, 1H), 3.73 (t, J=8.3 Hz, 1H), 3.02 (dd, J=14.0, 5.1 Hz, 1H), 2.65 (dd, J=13.9, 9.3 Hz, 1H), 2.44 (s, 3H), 2.19 (dd, J=14.8, 9.6 Hz, 1H), 1.86 (s, 1H), 1.56 (dt, J=15.3, 11.1 Hz, 3H), 1.25 (dd, J=14.7, 5.4 Hz, 1H), 1.07-0.97 (m, 7H), 0.94 (d, J=6.5 Hz, 3H), 0.64 (d, J=6.8 Hz, 4H), 0.50 (d, J=6.9 Hz, 3H), 0.33 (m, 1H), 0.16-0.07 (m, 1H), 0.01 (m, 1H), –0.09 (m, 1H).

LC-MS (ESI): $t_R$=6.50 min; m/z=962.23 [M+H]$^+$, 944.21 [M+H–H$_2$O]$^+$, 984.55 [M+Na]$^+$, calcd. for C$_{47}$H$_{63}$N$_9$O$_{13}$: 961.45.

Ahp25

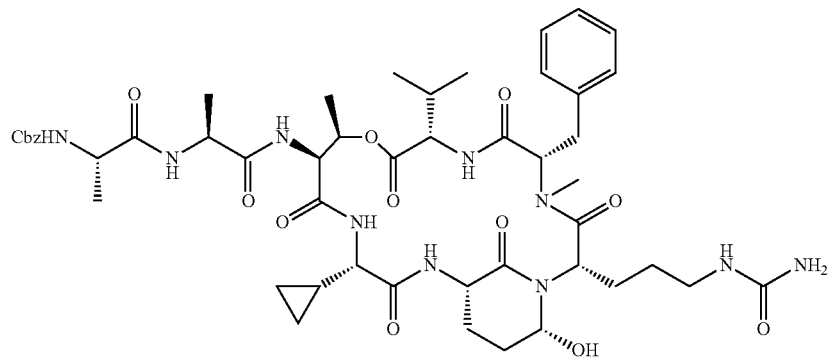 [SMILES: CC(C)[C@@H]1NC(=O)[C@H](Cc2ccccc2)N(C)C(=O)[C@H](CCCNC(N)=O)N2C(=O)[C@H](CC[C@H]2O)NC(=O)[C@H](C2CC2)NC(=O)[C@@H](NC(=O)[C@H](C)NC(=O)[C@H](C)NC(=O)OCc2ccccc2)[C@@H](C)OC1=O]

Ahp25 was synthesized via the 'general synthesis procedure for Ahp-cyclodepsipeptides'.

Yield: 1.1 mg (1.1 μmol, 1.1%) as a white solid.

$^1$H NMR (400 MHz, DMSO-d6): δ 8.53 (d, J=9.0 Hz, 1H), 8.05 (t, J=7.6 Hz, 1H), 7.88 (d, J=9.3 Hz, 1H), 7.51-7.43 (m, 2H), 7.44-7.14 (m, 11H), 5.99 (d, J=3.2 Hz, 1H), 5.50 (m, 1H), 5.34 (d, J=10.1 Hz, 2H), 5.01 (d, J=4.0 Hz, 3H), 4.95-4.86 (m, 2H), 4.72 (dd, J=9.5, 4.4 Hz, 1H), 4.59 (d, J=9.3 Hz, 1H), 4.42 (m, 3H), 4.08 (m, 2H), 3.94 (t, J=8.3 Hz, 1H), 2.88-2.76 (m, 1H), 2.72 (s, 3H), 2.67 (m, 3H), 2.33 (m, J=1.9 Hz, 1H), 2.22-2.03 (m, 1H), 1.75 (dd, J=17.8, 11.0 Hz, 3H), 1.22 (dt, J=13.0, 7.4 Hz, 11H), 1.09 (t, J=7.0 Hz, 2H), 0.84 (dd, J=17.5, 6.8 Hz, 6H), 0.72 (d, J=6.9 Hz, 3H), 0.55 (td, J=8.6, 4.0 Hz, 2H), 0.35 (m, 2H), 0.23 (m, 1H), 0.14 (m, 1H).

LC-MS (ESI): $t_R$=6.38 min; m/z=1005.33 [M+H]$^+$, 987.42 [M+H–H$_2$O]$^+$, 1027.64 [M+Na]$^+$, calcd. for $C_{49}H_{68}N_{10}O_{13}$: 1004.50.

Ahp26

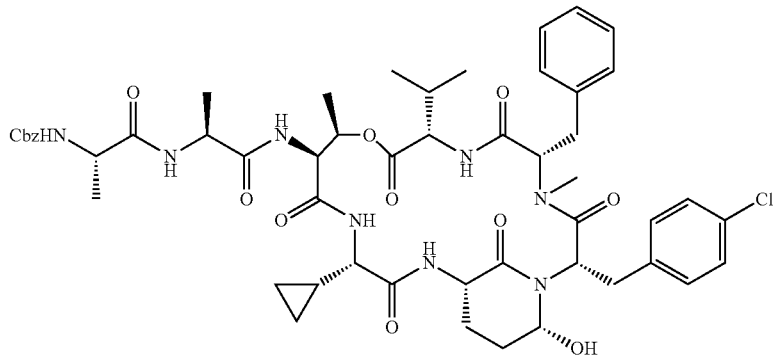 [SMILES: CC(C)[C@@H]1NC(=O)[C@H](Cc2ccccc2)N(C)C(=O)[C@H](Cc2ccc(Cl)cc2)N2C(=O)[C@H](CC[C@H]2O)NC(=O)[C@H](C2CC2)NC(=O)[C@@H](NC(=O)[C@H](C)NC(=O)[C@H](C)NC(=O)OCc2ccccc2)[C@@H](C)OC1=O]

Ahp26 was synthesized via the 'general synthesis procedure for Ahp-cyclodepsipeptides'.

Yield: 0.5 mg (0.5 μmol, 0.5%) as a white solid.

$^1$H NMR (400 MHz, DMSO-d6): δ 8.49 (d, J=8.8 Hz, 1H), 8.03 (d, J=7.4 Hz, 1H), 7.84 (d, J=9.3 Hz, 1H), 7.50-7.18 (m, 14H), 7.06 (d, J=8.8 Hz, 1H), 6.82-6.75 (m, 2H), 6.07 (d, J=3.1 Hz, 1H), 5.42 (q, J=6.6 Hz, 1H), 5.05 (s, 1H), 5.02 (s, 2H), 4.92 (dd, J=11.5, 2.9 Hz, 1H), 4.73-4.63 (m, 2H), 4.55 (d, J=9.4 Hz, 1H), 4.45 (p, J=7.0 Hz, 1H), 4.08 (m, 1H), 3.80 (t, J=8.4 Hz, 1H), 3.68 (dt, J=12.1, 8.4 Hz, 1H), 3.14 (d, J=5.5 Hz, 1H), 2.90-2.81 (m, 1H), 2.79 (s, 3H), 2.44-2.30 (m, 1H), 2.08 (h, J=6.9 Hz, 1H), 1.64 (dt, J=24.6, 16.9 Hz, 3H), 1.26-1.19 (m, 8H), 1.16 (d, J=6.6 Hz, 3H), 0.90-0.84 (m, 3H), 0.76-0.70 (m, 4H), 0.51 (m, 1H), 0.31 (m, 1H), 0.20 (dt, J=9.8, 4.8 Hz, 1H), 0.09 (dt, J=9.7, 4.9 Hz, 1H).

LC-MS (ESI): $t_R$=6.51 min; m/z=1029.02 [M+H]$^+$, 1011.39 [M+H–H$_2$O]$^+$, 1051.63 [M+Na]$^+$, calcd. for $C_{52}H_{65}ClN_8O_{12}$: 1028.44.

Ahp27

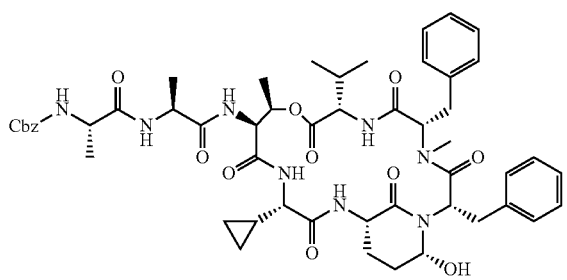 [SMILES: CC(C)[C@@H]1NC(=O)[C@H](Cc2ccccc2)N(C)C(=O)[C@H](Cc2ccccc2)N2C(=O)[C@H](CC[C@H]2O)NC(=O)[C@H](C2CC2)NC(=O)[C@@H](NC(=O)[C@H](C)NC(=O)[C@H](C)NC(=O)OCc2ccccc2)[C@@H](C)OC1=O]

Ahp27 was synthesized via the 'general synthesis procedure for Ahp-cyclodepsipeptides'.

Yield: 2.1 mg (2.1 μmol, 1.1%) as a white solid.

$^1$H NMR (400 MHz, DMSO-d$_6$) δ=−0.17−−0.06 (m, 1H), −0.04-0.06 (m, 1H), 0.06-0.18 (m, 1H), 0.25-0.37 (m, 4.5, 1H), 0.50-0.56 (d, J=6.9, 3H), 0.64-0.71 (d, J=6.9, 3H), 0.83-1.07 (m, 11H), 1.26-1.38 (t, J=13.6, 1H), 1.42-1.53 (m, 3H), 1.83-1.96 (m, 1H), 2.11-2.25 (m, 1H), 2.62-2.72 (m, 2H), 3.00-3.08 (d, J=12.6, 1H), 3.32-3.43 (m, 1H), 3.54-3.64 (t, J=8.5, 1H), 3.83-3.95 (p, J=7.1, 1H), 4.20-4.40 (m, 2H), 4.47-4.58 (m, 2H), 4.76-4.87 (m, 4H), 5.16-5.26 (q, J=6.5, 1H), 5.81-5.86 (d, J=3.2, 1H), 6.54-6.62 (m, 2H), 6.78-6.86 (d, J=8.8, 1H), 6.86-7.09 (m, 6H), 7.09-7.32 (m, 10H), 7.61-7.68 (d, J=9.3, 1H), 7.78-7.87 (d, J=7.4, 1H), 8.27-8.34 (d, J=8.9, 1H).

Ahp28

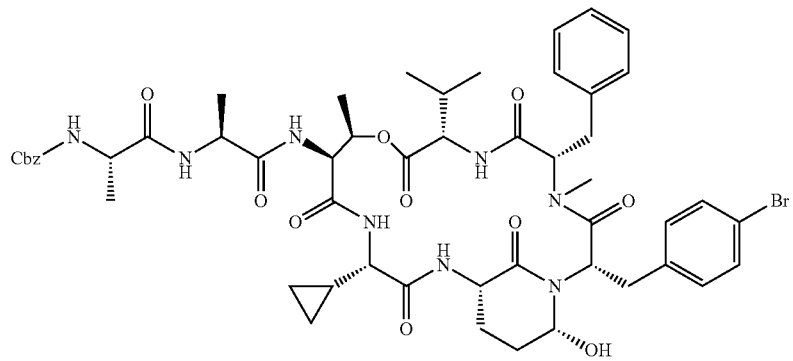 [SMILES: CC(C)[C@@H]1NC(=O)[C@H](Cc2ccccc2)N(C)C(=O)[C@H](Cc2ccc(Br)cc2)N2C(=O)[C@H](CC[C@H]2O)NC(=O)[C@H](C2CC2)NC(=O)[C@@H](NC(=O)[C@H](C)NC(=O)[C@H](C)NC(=O)OCc2ccccc2)[C@@H](C)OC1=O]

Ahp28 was synthesized via the 'general synthesis procedure for Ahp-cyclodepsipeptides'.

Yield: 1.88 mg (1.6 μmol, 0.88%) as a white solid.

LC-MS (ESI): t$_R$=8.94 min; m/z=1072.83 [M+H]$^+$, 1074.80 [M+H]$^+$ calcd. for C$_{52}$H$_{65}$BrN$_8$O$_{12}$: 1072.39, 1074.39.

Ahp29

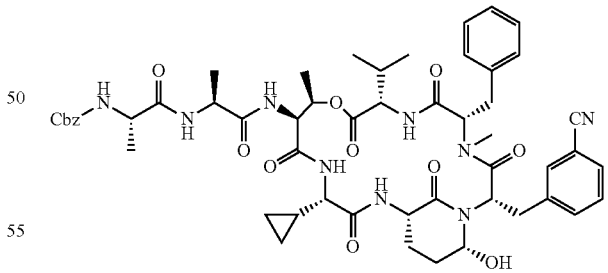

Ahp29 was synthesized via the 'general synthesis procedure for Ahp-cyclodepsipeptides'.

Yield: 14.2 mg (13.9 μmol, 7.0%) as a white solid.

$^1$H NMR (400 MHz, DMSO-d$_6$) δ=−0.07-0.03 (m, 1H), 0.09-0.26 (m, 2H), 0.28-0.40 (m, 1H), 0.60-0.74 (m, 6H), 0.82-1.17 (m, 11H), 1.18-1.36 (m, 4H), 1.44-1.61 (s, 2H), 1.97-2.10 (m, 1H), 2.36-2.51 (m, 2H), 2.82-2.97 (m, 1H), 3.18-3.25 (m, 2H), 3.42-3.53 (t, J=7.9, 1H), 3.87-3.97 (m, 1H), 3.96-4.01 (m, 1H), 4.04-4.11 (t, J=6.9, 1H), 4.18-4.24

(q, J=7.1, 1H), 4.29-4.33 (t, J=4.9, 1H), 4.37-4.51 (m, 2H), 4.79-4.90 (d, J=2.5, 2H), 4.99-5.21 (m, 2H), 6.75-6.83 (d, J=8.5, 1H), 6.86-6.95 (m, 1H), 6.95-7.02 (m, 2H), 7.10-7.34 (m, 10H), 7.36-7.40 (s, 1H), 7.47-7.51 (m, 1H), 7.71-7.78 (t, J=7.8, 1H), 7.84-7.91 (d, J=7.3, 1H), 8.37-8.43 (d, J=7.7, 1H), 8.51-8.58 (d, J=6.2, 1H).

Ahp30

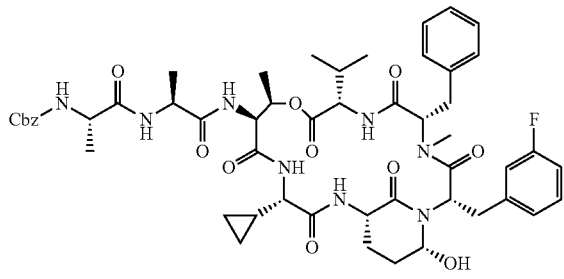 [SMILES: CC(C)[C@@H]1NC(=O)[C@H](Cc2ccccc2)N(C)C(=O)[C@H](Cc2cccc(F)c2)N2C(=O)[C@H](CC[C@H]2O)NC(=O)[C@H](C2CC2)NC(=O)[C@@H](NC(=O)[C@H](C)NC(=O)[C@H](C)NC(=O)OCc2ccccc2)[C@@H](C)OC1=O]

Ahp30 was synthesized via the 'general synthesis procedure for Ahp-cyclodepsipeptides'.

Yield: 6.3 mg (6.2 μmol, 3.1%) as a white solid.

$^1$H NMR (400 MHz, DMSO-d$_6$) δ=−0.07-0.04 (m, 1H), 0.09-0.26 (m, 2H), 0.29-0.40 (m, 1H), 0.62-0.72 (t, J=6.7, 6H), 0.78-0.85 (q, J=7.5, 1H), 0.85-0.94 (m, 2H), 0.94-0.99 (d, J=6.5, 3H), 1.00-1.06 (d, J=7.2, 5H), 1.06-1.09 (d, J=4.6, 1H), 1.19-1.37 (m, 3H), 1.41-1.58 (m, 2H), 1.95-2.08 (h, J=6.8, 1H), 2.25-2.32 (m, 0H), 2.44-2.51 (m, 1H), 2.79-2.95 (m, 2H), 3.41-3.50 (t, J=7.9, 1H), 3.84-3.96 (p, J=7.2, 1H), 3.96-4.15 (m, 3H), 4.16-4.28 (m, 1H), 4.28-4.35 (t, J=4.9, 1H), 4.37-4.56 (m, 2H), 4.79-4.91 (d, J=2.9, 2H), 4.99-5.15 (m, 2H), 6.72-6.87 (m, 4H), 6.87-6.96 (m, 1H), 6.96-7.02 (m, 2H), 7.05-7.23 (m, 8H), 7.24-7.34 (m, 1H), 7.66-7.78 (d, J=8.7, 1H), 7.84-7.91 (d, J=7.4, 1H), 8.37-8.44 (d, J=7.7, 1H), 8.50-8.63 (m, 1H).

Ahp31

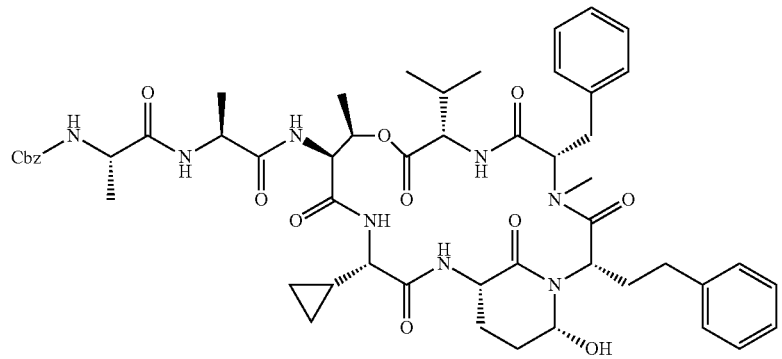 [SMILES: CC(C)[C@@H]1NC(=O)[C@H](Cc2ccccc2)N(C)C(=O)[C@H](CCc2ccccc2)N2C(=O)[C@H](CC[C@H]2O)NC(=O)[C@H](C2CC2)NC(=O)[C@@H](NC(=O)[C@H](C)NC(=O)[C@H](C)NC(=O)OCc2ccccc2)[C@@H](C)OC1=O]

Ahp31 was synthesized via the 'general synthesis procedure for Ahp-cyclodepsipeptides'.

Yield: 6.7 mg (6.7 μmol, 3.4%) as a white solid.

$^1$H NMR (400 MHz, DMSO-d$_6$) δ=−0.02-0.13 (d, J=14.2, 1H), 0.15-0.26 (m, 1H), 0.35-0.54 (m, 3H), 0.69-0.78 (m, 3H), 0.79-0.85 (d, J=6.9, 3H), 0.86-0.93 (m, 1H), 1.07-1.13 (d, J=6.2, 3H), 1.21-1.26 (d, J=7.2, 3H), 1.26-1.30 (s, 8H), 1.30-1.35 (d, J=7.0, 2H), 1.53-1.64 (m, 1H), 1.75-1.87 (m, 1H), 2.01-2.08 (m, 1H), 2.28-2.35 (m, 1H), 2.74-2.81 (d, J=4.8, 3H), 2.87-2.96 (m, 1H), 3.80-3.91 (d, J=13.5, 1H), 3.98-4.05 (d, J=8.8, 1H), 4.25-4.37 (m, 1H), 4.45-4.58 (m, 10.4, 2H), 4.59-4.74 (m, 3H), 4.92-4.94 (s, 2H), 5.10-5.17 (d, J=5.2, 1H), 5.43-5.53 (t, J=5.2, 1H), 5.73-5.81 (d, J=5.6, 1H), 6.83-6.94 (t, J=7.4, 1H), 7.02-7.42 (m, 15H), 7.52-7.61 (d, J=9.9, 1H), 8.30-8.37 (d, J=9.5, 1H), 8.49-8.57 (d, J=7.5, 1H), 8.78-8.80 (s, 1H).

LC-MS (ESI): t$_R$=8.30 min; m/z=1009.43 [M+H]$^+$, 1031.45 [M+Na]$^+$; calcd. for C$_{53}$H$_{68}$N$_8$O$_{12}$: 1008.50.

Ahp32

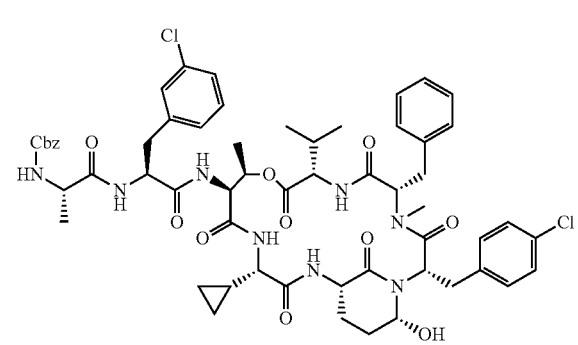 [SMILES: CC(C)[C@@H]1NC(=O)[C@H](Cc2ccccc2)N(C)C(=O)[C@H](Cc2ccc(Cl)cc2)N2C(=O)[C@H](CC[C@H]2O)NC(=O)[C@H](C2CC2)NC(=O)[C@@H](NC(=O)[C@H](Cc2cccc(Cl)c2)NC(=O)[C@H](C)NC(=O)OCc2ccccc2)[C@@H](C)OC1=O]

Ahp32 was synthesized via the 'general synthesis procedure for Ahp-cyclodepsipeptides'.

Yield: 0.4 mg (0.35 μmol, 0.18%) as a white solid.

$^1$H NMR (400 MHz, DMSO-d$_6$) δ=0.07-0.17 (d, J=5.0, 1H), 0.21-0.35 (m, 2H), 0.47-0.59 (m, 1H), 0.71-0.76 (d, J=6.9, 2H), 0.81-0.90 (m, 7H), 1.13-1.16 (d, J=7.1, 3H), 1.36-1.52 (d, J=6.9, 2H), 1.60-1.76 (s, 2H), 1.96-2.02 (m, 1H), 2.05-2.12 (s, 2H), 2.77-2.88 (d, J=20.0, 5H), 3.00-3.11 (d, J=13.1, 1H), 3.64-3.74 (m, 1H), 3.80-3.89 (t, J=8.4, 1H), 3.98-4.05 (t, J=7.4, 1H), 4.56-4.61 (d, J=9.2, 1H), 4.63-4.70 (s, 1H), 4.71-4.77 (m, 1H), 4.77-4.84 (s, 1H), 4.93-5.09 (m, 4H), 5.29-5.37 (t, J=4.7, 1H), 5.41-5.50 (d, J=6.8, 1H), 6.05-6.12 (d, J=3.0, 1H), 6.60-6.68 (s, 1H), 6.73-6.85 (d, J=8.3, 2H), 7.05-7.11 (d, J=8.9, 1H), 7.13-7.45 (m, 16H), 7.46-7.52 (d, J=9.6, 1H), 7.81-7.89 (d, J=8.2, 1H), 8.17-8.25 (d, J=9.1, 1H), 8.49-8.56 (d, J=9.0, 1H).

LC-MS (ESI): t$_R$=9.71 min; m/z=1139.53 [M+H]$^+$, 1162.27 [M+Na]$^+$; calcd. for C$_{58}$H$_{68}$O$_2$N$_8$O$_{12}$: 1138.43.

Ahp33

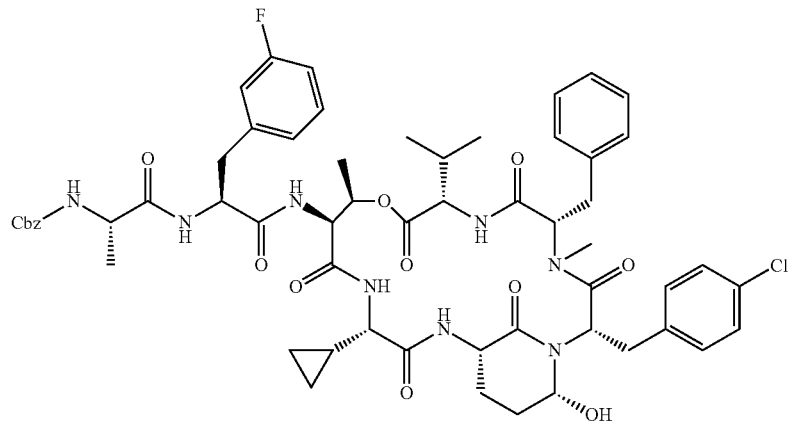 [SMILES: CC(C)[C@@H]1NC(=O)[C@H](Cc2ccccc2)N(C)C(=O)[C@H](Cc2ccc(Cl)cc2)N2C(=O)[C@H](CC[C@H]2O)NC(=O)[C@H](C2CC2)NC(=O)[C@@H](NC(=O)[C@H](Cc2cccc(F)c2)NC(=O)[C@H](C)NC(=O)OCc2ccccc2)[C@@H](C)OC1=O]

Ahp33 was synthesized via the 'general synthesis procedure for Ahp-cyclodepsipeptides'.

Yield: 0.3 mg (0.27 μmol, 0.13%) as a white solid.

$^1$H NMR (400 MHz, DMSO-$d_6$) δ=0.08-0.15 (d, J=6.5, 1H), 0.19-0.27 (m, 1H), 0.28-0.37 (m, 1H), 0.50-0.58 (d, J=6.0, 1H), 0.65-0.76 (d, J=6.8, 2H), 0.82-0.91 (q, J=7.0, 7H), 1.14-1.18 (d, J=7.4, 3H), 1.52-1.71 (s, 4H), 1.95-2.01 (s, 1H), 2.05-2.12 (s, 1H), 2.14-2.21 (t, J=7.3, 1H), 2.74-2.83 (d, J=15.7, 3H), 2.83-2.93 (m, 2H), 3.04-3.13 (d, J=12.3, 1H), 3.63-3.76 (m, 1H), 3.78-3.89 (t, J=8.5, 1H), 3.98-4.08 (t, J=7.3, 1H), 4.55-4.62 (d, J=9.1, 1H), 4.63-4.71 (d, J=10.1, 1H), 4.73-4.78 (dd, J=9.6, 4.4, 1H), 4.78-4.85 (s, 1H), 4.89-4.96 (d, J=11.3, 1H), 5.01-5.08 (d, J=24.1, 2H), 5.25-5.50 (m, 2H), 6.04-6.11 (d, J=3.1, 1H), 6.75-6.83 (d, J=8.2, 2H), 6.93-7.53 (m, 17H), 7.79-7.88 (d, J=7.9, 1H), 8.15-8.22 (d, J=9.3, 1H), 8.49-8.58 (d, J=8.9, 1H).

LC-MS (ESI): $t_R$=9.44 min; m/z=1122.61 [M+H]$^+$, 1145.30 [M+Na]$^+$; calcd. for $C_{68}H_{68}ClFN_8O_{12}$: 1122.46.

Ahp34

Ahp34 was synthesized via the 'general synthesis procedure for Ahp-cyclodepsipeptides'.

Yield: 0.96 mg (0.86 μmol, 0.42%) as a white solid.

$^1$H NMR (400 MHz, DMSO-$d_6$) δ=−0.10−−0.01 (m, 1H), 0.07-0.15 (m, 1H), 0.29-0.35 (d, J=7.9, 2H), 0.64-0.72 (d, J=6.8, 3H), 0.76-0.81 (d, J=6.9, 3H), 0.81-0.89 (t, J=6.6, 3H), 0.92-1.00 (m, 1H), 1.03-1.08 (d, J=6.1, 2H), 1.08-1.17 (s, 2H), 1.19-1.23 (s, 4H), 1.39-1.55 (d, J=8.2, 2H), 1.78-2.01 (s, 2H), 2.03-2.14 (m, 2H), 2.22-2.30 (m, 1H), 2.73-2.81 (d, J=9.6, 3H), 2.85-2.94 (d, J=12.9, 1H), 3.65-3.71 (d, J=8.9, 1H), 3.84-3.94 (d, J=13.4, 1H), 4.19-4.25 (d, J=9.1, 1H), 4.25-4.42 (dt, J=31.6, 7.8, 2H), 4.59-4.71 (m, 2H), 4.80-4.89 (d, J=12.2, 1H), 4.90-4.94 (s, 1H), 4.99-5.06 (s, 3H), 5.35-5.42 (d, J=5.1, 1H), 5.66-5.70 (d, J=5.6, 1H), 6.95-7.03 (q, J=8.0, 7.0, 2H), 7.08-7.31 (m, 20H), 7.42-7.48 (d, J=9.9, 1H), 8.28-8.35 (d, J=9.5, 1H), 8.48-8.53 (d, J=3.8, 1H), 8.56-8.63 (d, J=7.5, 1H), 8.64-8.73 (d, J=9.8, 1H).

LC-MS (ESI): $t_R$=9.94 min; m/z=1118.79 [M+H]$^+$, 1141.37 [M+Na]$^+$; calcd. for $C_{59}H_{71}ClN_8O_{12}$: 1118.49.

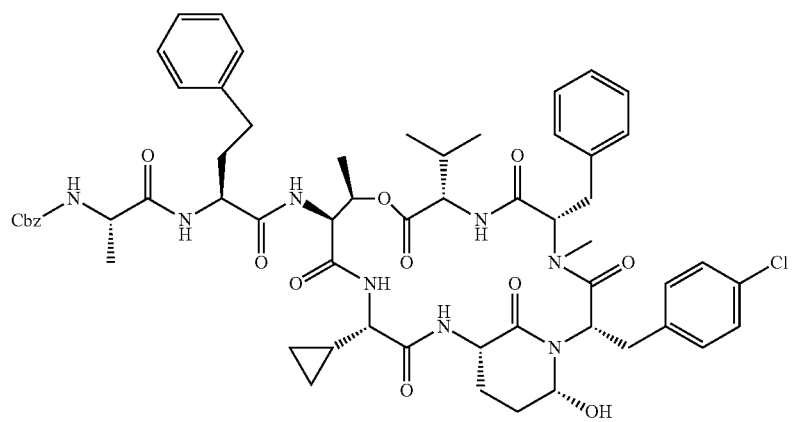 [SMILES: CC(C)[C@@H]1NC(=O)[C@H](Cc2ccccc2)N(C)C(=O)[C@H](Cc2ccc(Cl)cc2)N2C(=O)[C@H](CC[C@H]2O)NC(=O)[C@H](C2CC2)NC(=O)[C@@H](NC(=O)[C@H](CCc2ccccc2)NC(=O)[C@H](C)NC(=O)OCc2ccccc2)[C@@H](C)OC1=O]

Ahp35

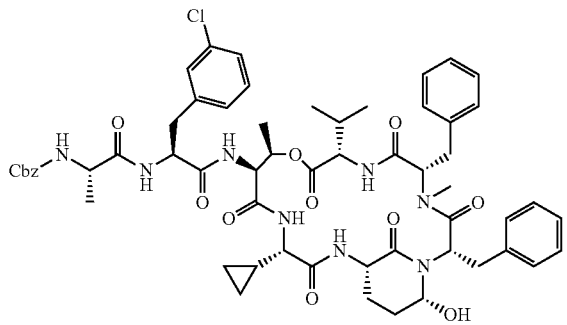

Ahp35 was synthesized via the 'general synthesis procedure for Ahp-cyclodepsipeptides'.

Yield: 0.81 mg (0.73 µmol, 0.37%) as a white solid.

$^1$H NMR (400 MHz, DMSO-d$_6$) δ=−0.16--−0.08 (s, 1H), −0.05-0.04 (d, J=5.4, 1H), 0.12-0.21 (d, J=7.9, 2H), 0.51-0.58 (d, J=6.8, 2H), 0.62-0.76 (m, 8H), 0.84-1.05 (m, 10H), 1.26-1.43 (s, 3H), 1.49-1.61 (m, 2H), 1.79-1.89 (s, 3H), 1.91-1.92 (s, 1H), 2.56-2.63 (s, 3H), 2.63-2.74 (d, J=30.4, 3H), 3.47-3.56 (d, J=12.9, 1H), 3.62-3.69 (m, 1H), 3.83-3.91 (q, J=7.1, 2H), 3.91-4.02 (t, J=7.7, 1H), 4.07-4.15 (d, J=9.2, 1H), 4.40-4.46 (d, J=8.9, 1H), 4.50-4.55 (m, 2H), 4.78-4.80 (s, 1H), 4.81-4.92 (d, J=14.5, 3H), 4.94-5.02 (d, J=6.7, 1H), 5.15-5.20 (t, J=4.8, 1H), 5.22-5.29 (t, J=5.0, 1H), 5.50-5.54 (d, J=5.5, 1H), 5.58-5.61 (s, 2H), 6.60-6.64 (d, J=7.4, 1H), 6.70-6.78 (d, J=7.4, 1H), 6.90-7.00 (d, J=6.7, 5H), 7.02-7.11 (m, 8H), 7.14-7.22 (s, 5H), 7.52-7.66 (d, J=9.6, 1H), 8.09-8.20 (t, J=9.8, 2H), 8.31-8.35 (d, J=3.7, 1H), 8.50-8.63 (d, J=9.8, 1H).

LC-MS (ESI): t$_R$=9.52 min; m/z=1104.93 [M+H]$^+$, 1128.39 [M+Na]$^+$; calcd. for C$_{58}$H$_{69}$ClN$_8$O$_{12}$: 1104.47.

Ahp36

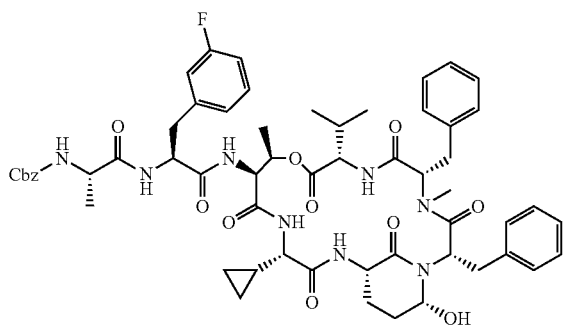 [SMILES: CC(C)[C@@H]1NC(=O)[C@H](Cc2ccccc2)N(C)C(=O)[C@H](Cc2ccccc2)N2C(=O)[C@H](CC[C@H]2O)NC(=O)[C@H](C2CC2)NC(=O)[C@@H](NC(=O)[C@H](Cc2cccc(F)c2)NC(=O)[C@H](C)NC(=O)OCc2ccccc2)[C@@H](C)OC1=O]

Ahp36 was synthesized via the 'general synthesis procedure for Ahp-cyclodepsipeptides'.

Yield: 0.50 mg (0.46 µmol, 0.23%) as a white solid.

$^1$H NMR (400 MHz, DMSO-d$_6$) δ=−0.02-0.07 (s, 1H), 0.07-0.18 (m, 1H), 0.20-0.41 (d, J=8.1, 4H), 0.44-0.55 (d, J=8.7, 1H), 0.65-0.76 (m, 4H), 0.76-0.91 (m, 7H), 0.99-1.18 (m, 9H), 1.21-1.34 (s, 5H), 1.37-1.58 (m, 3H), 1.58-1.72 (d, J=18.0, 2H), 1.89-2.22 (m, 3H), 2.22-2.35 (m, 2H), 2.69-2.81 (m, 4H), 2.81-2.93 (d, J=18.7, 3H), 2.93-3.09 (m, 2H), 3.12-3.21 (d, J=4.4, 4H), 3.52-3.70 (m, 2H), 3.73-3.86 (m, 2H), 3.94-4.16 (m, 4H), 4.16-4.31 (m, 2H), 4.53-4.63 (d, J=9.5, 1H), 4.64-4.76 (m, 3H), 4.86-5.08 (m, 6H), 5.36-5.46 (m, 2H), 5.65-5.70 (d, J=5.5, 1H), 5.99-6.08 (s, 1H), 6.72-6.82 (t, J=6.8, 2H), 6.83-7.48 (m, 21H), 7.68-7.74 (d, J=9.6, 1H), 7.79-7.86 (d, J=8.0, 1H), 7.86-7.94 (d, J=8.0, 1H), 8.13-8.23 (d, J=9.2, 1H), 8.23-8.37 (t, J=8.4, 2H), 8.52-8.64 (m, 1H), 8.66-8.74 (d, J=9.8, 1H).

LC-MS (ESI): t$_R$=9.20 min; m/z=1088.84 [M+H]$^+$, 1111.41 [M+Na]$^+$; calcd. for C$_{58}$H$_{69}$FN$_8$O$_{12}$: 1088.50.

Ahp37

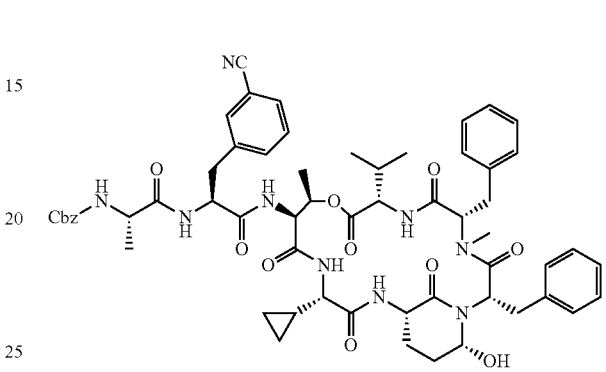

Ahp37 was synthesized via the 'general synthesis procedure for Ahp-cyclodepsipeptides'.

Yield: 0.87 mg (0.79 µmol, 0.40%) as a white solid.

$^1$H NMR (400 MHz, DMSO-d$_6$) δ=0.04-0.13 (s, 1H), 0.18-0.27 (d, J=4.9, 1H), 0.28-0.36 (d, J=8.1, 1H), 0.45-0.57 (s, 1H), 0.63-0.75 (m, 2H), 0.77-0.90 (m, 3H), 1.07-1.19 (m, 3H), 1.20-1.31 (s, 4H), 1.42-1.56 (s, 2H), 1.59-1.75 (d, J=12.9, 2H), 1.93-2.03 (m, 2H), 2.04-2.12 (s, 4H), 2.76-2.81 (s, 1H), 2.82-2.99 (d, J=13.7, 3H), 3.78-3.86 (s, 1H), 3.97-4.09 (t, J=7.4, 2H), 4.55-4.60 (d, J=8.9, 1H), 4.64-4.77 (m, 2H), 4.79-4.86 (s, 1H), 4.92-4.95 (s, 1H), 4.95-5.05 (m, 2H), 5.30-5.36 (s, 1H), 5.37-5.48 (d, J=7.0, 1H), 5.65-5.71 (d, J=5.0, 1H), 5.72-5.79 (s, 1H), 6.00-6.08 (s, 1H), 6.59-6.74 (s, 2H), 6.75-6.80 (d, J=7.3, 1H), 6.99-7.74 (m, 11H), 7.76-7.93 (d, J=7.6, 2H), 8.19-8.32 (dd, J=17.5, 8.8, 1H), 8.49-8.56 (s, 1H), 8.66-8.72 (s, 1H).

LC-MS (ESI): t$_R$=8.84 min; m/z=1095.83 [M+H]$^+$, 1118.44 [M+Na]$^+$; calcd. for C$_{59}$H$_{69}$N$_9$O$_{12}$: 1095.51.

Example 3: Biochemical Determination of the Protease Activity

Enzymes

The following enzymes were purchased from commercial distributors: humane neutrophil elastase (Enzo Life Sciences; BML-SE284), human pancreas chymotrypsin (Sigma-Aldrich; SRP6509-100, Lot #2D207538) and bovine pancreas trypsin (Sigma-Aldrich; T1426).

Alternatively, the enzymes HTRA1 (aa 158-480, n-terminal StrepII-tag, from pET21d backbone), HTRA2 (aa 134-458, n-terminal His-tag, form pET28 backbone), and HTRA3 (aa 111-436, c-terminal His-tag, from pET21d backbone) were expressed and purified as described in the art.

Chromogenic Enzyme Activity Assays

In general, proteolytic activity was tested by monitoring the cleavage of the specific chromogenic substrate at 405 nm wavelength for 60 or 120 minutes in a Tecan Spark M10 or Tecan Genios Pro plate reader at 37° C. After optimization of assay conditions, every enzyme was tested in 100 µL final volume with 500 µM chromogenic substrate. Where applicable, inhibitor and enzyme were pre-incubated for 10 minutes in the buffer at 37° C. before substrate addition. Compounds were pre-solved in DMSO and used in the assays with a final DMSO concentration of 3% (v/v).

$IC_{50}$ and $K_i$ values, enzyme assays were performed with differing inhibitor concentrations (2.5 nM to 20/200 µM), specific activities were calculated, and plotted against log inhibitor concentrations in GraphPad Prism 5 software. One

TABLE 1

Overview on biochemical assay conditions.

| enzyme | final conc. | buffer | substrate | $K_M$ |
|---|---|---|---|---|
| human neutrophil elastase | 50 nM | 100 mM HEPES, 500 mM, NaCl, 0.05% (v/v) Tween-20, pH 7.25 | AAPV-pNA (Sigma-Aldrich; M4765) | 256.8 µM |
| human pancreas chymotrypsin | 100 nM | 100 mM HEPES, 500 mM NaCl, 0.05% (v/v) Tween-20, pH 7.25 | AAF-pNA (Sigma-Aldrich; A9148) | 1389 µM |
| bovine pancreas trypsin | 100 nM | 150 mM NaH2PO4, 380 mM NaCl, pH 8.3 | Nα-Benzoyl-DL-Arg-pNA × HCl (Sigma-Aldrich; #B4875) | n.d. |
| HTRA1 | 1 µM | 150 mM NaH2PO4, 380 mM NaCl, pH 8.3 | VFNTLPMMG KASPV-pNA | 269 µM |
| HTRA2 | 1 µM | 150 mM NaH2PO4, 380 mM NaCl, pH 8.3 | VFNTLPMMG KASPV-pNA | 1347 µM |
| HTRA3 | 1 µM | 500 mM NaH2PO4, pH 8.0 | VFNTLPMMG KASPV-pNA | 388.2 µM |

The determined specific activities (sa) were derived from duplicate measurements and calculated as $$sa = \Delta OD405 \times V/(m \times \varepsilon \times t)$$

($\Delta OD405$: change of absorption at $\lambda=405$ nm over specific time; V: final volume of reaction, m: amount of protease (mg), $\varepsilon$: molar extinction coefficient of para-nitroaniline, t: time interval for measurement).

site—Fit $K_i$ and One site—Fit $logIC_{50}$ (software built-in) analysis were used to calculate $IC_{50}$ and $K_i$ values.

Results

1. Amino Acid Variations at Different Positions

After chemical synthesis of Ahp1-Ahp8, these compounds were analyzed in biochemical assays (Table 2).

TABLE 2

Biochemical inhibition data for synthesized Ahp-cyclodepsipeptides.

| | Ki [µM] | | | | | |
|---|---|---|---|---|---|---|
| Cpd | Chymo-trypsin [a] | Elastase [b] | Trypsin [c] | HTRA1 [d] | HTRA2 [d] | HTRA3 [d] |
| Ahp1 | >50 | 0.019 ± 0.003 | >50 | 8.2 ± 2.7 | 4.1 ± 0.4 | 3.0 ± 0.5 |
| Ahp2 | 0.37 ± 0.08 | >50 | >50 | >50 | >50 | >50 |
| Ahp3 | >50 | 0.21 ± 0.06 | >50 | >50 | 0.27 ± 0.07 | 3.1 ± 0.6 |
| Ahp4 | >50 | 0.33 ± 0.06 | >50 | >50 | 0.49 ± 0.11 | >50 |
| Ahp5 | >50 | 6.4 ± 1.2 | >50 | >50 | >50 | >50 |
| Ahp6 | >50 | 8.0 ± 1.8 | >50 | 10.3 ± 3.0 | 2.1 ± 0.3 | >50 |
| Ahp7 | >50 | 0.11 ± 0.02 | >50 | >50 | 6.9 ± 1.5 | >50 |
| Ahp8 | >50 | 0.32 ± 0.05 | >50 | >50 | 2.3 ± 0.2 | 9.5 ± 0.9 |
| Ahp9 | 2.1 ± 0.2 | 3.4 ± 1.1 | >50 | >50 | 2.8 ± 0.7 | >50 |
| Ahp10 | >50 | 0.018 ± 0.004 | >50 | 2.4 ± 0.6 | 0.26 ± 0.03 | 0.48 ± 0.07 |
| Ahp11 | | 0.007 | | >50 | 4.0 | 9.5 |

[a] Human pancreas chymotrypsin,
[b] human neutrophil elastase,
[c] bovine trypsin,
[d] human HTRA proteases.

In order to determine $K_M$ values, the assays were performed as described but with differing substrate concentrations (10 µM to 4 mM). Specific activity was calculated and plotted against substrate concentrations in GraphPad Prism 5 software. Michaelis-Menten (software built-in) analysis was used to calculate the KM values. In order to determine As expected, the change of the P1 position from Val to Phe in Ahp2 significantly reduced elastase and HTRA1-HTRA3 inhibition but enhanced chymotrypsin inhibition. The inhibition profile for elastase furthermore revealed that despite the preference for Val in P1, many other structural changes were well tolerated. Besides Ahp2, all generated compounds were low μM or even sub-μM elastase inhibitors, including Ahp7 with its N-MeAla residue at P3', thereby demonstrating that the structurally conserved N-Me aromatic amino acids are not required to maintain high inhibitory potency. For the HTRA proteases, the inhibitory profile was much more sensitive. Besides Ahp1, HTRA1 and HTRA3 were inhibited only by Ahp6 and Ahp3/Ahp8, respectively, while other substitutions led to inactive compounds. HTRA2 was inhibited by all Ahp-cyclodepsipeptides except Ahp2, and the derivative Ahp4 was more than ten-fold more potent than Ahp1, thus displaying sub-μM inhibition potencies. Encouraged by these results, we performed another round of single substitutions at selected positions of Ahp1, using findings from a proteome-wide substrate screen that revealed a distinct selectivity for Leu at P2 and the finding that the P1 selectivity is not restricted to Val but may also accommodate Leu. We therefore synthesized three further derivatives Ahp9 with Leu at P1, Ahp10 with the non-proteinogenic amino acid (3-OH)Leu at P2, and Ahp11 lacking P4. Biochemical evaluation of these compounds revealed that Ahp9 displayed slightly better HTRA2 inhibitory properties than Ahp1. More intriguingly however, incorporation of (3-OH)Leu at P2 in Ahp10 led to a 15-fold more active compound with a sub-μM $K_i$ (Table 2). Of note, this structural change also lowered the $K_i$ for HTRA1 and elastase, thereby further demonstrating the potential of the Ahp-cyclodepsipeptide scaffold for generating tailored serine protease inhibitors. Ahp11 showed moderate inhibition of HTRA2 and HTRA3, but no inhibition of HTRA1.

2. Amino Acid Variations at Position P1

In a further series, Ahp-cyclodepsipeptides with various different amino acids at the P1 position were synthesized. After chemical synthesis of Ahp13-Ahp21, these compounds were analyzed in biochemical assays (Table 3).

TABLE 3

Biochemical inhibition data for synthesized Ahp-cyclodepsipeptides.

| Compound | Ki [μM] | | | |
|---|---|---|---|---|
| | HTRA1 [a] | HTRA2 [a] | HTRA3 [a] | Elastase [b] |
| Ahp13 | 4.26 | 0.26 | 0.98 | 0.026 |
| Ahp14 | 2.97 | 0.70 | 1.46 | 0.47 |
| Ahp15 | 7.0 | 0.69 | >50 | 0.13 |
| Ahp16 | >50 | >50 | 0.50 | 50 |
| Ahp17 | >50 | 1.38 | 0.84 | 0.16 |
| Ahp18 | >50 | | 17.9 | 0.20 |
| Ahp19 | 1.24 | 1.11 | 0.74 | 1.93 |
| Ahp20 | >50 | >50 | 8.3 | 4.32 |
| Ahp21 | >50 | >50 | >50 | >50 |

[a] human HTRA proteases,
[b] human neutrophil elastase

Most of the variants, except for Ahp21, showed protease inhibition against at least one of HTRA1-3. Peptides Ahp13, Ahp14 and Ahp19 even had enhanced inhibitory activity for all HTRA proteases. An especially strong inhibitory effect was demonstrated for Ahp19, which has a cyclopropyl group as side chain at position P1.

3. Ahp-Cyclodepsipeptides with a Cyclopropyl Amino Acid at Position P1

Different Ahp-cyclodepsipeptides with an amino acid having a cyclopropyl side chain at position P1 were synthesized. After chemical synthesis of Ahp22-Ahp37, these compounds were analyzed in biochemical assays (Table 4).

TABLE 4

Biochemical inhibition data for synthesized Ahp-cyclodepsipeptides.

| Compound | Ki [μM] HTRA1 [a] |
|---|---|
| Ahp22 | 5.2 |
| Ahp24 | 1.66 |
| Ahp25 | 0.70 |
| Ahp26 | 0.065 |
| Ahp27 | 0.95 |
| Ahp28 | 2.8 |
| Ahp29 | 1.8 |
| Ahp30 | 3.0 |
| Ahp33 | 0.61 |
| Ahp34 | 43.4 |
| Ahp35 | 6.3 |
| Ahp36 | 1.4 |
| Ahp37 | 1.4 |

[a] human HTRA proteases

In view of the strong inhibitory effect of Ahp19, variants of this peptide with different amino acids at position P2' and P3 were generated and tested for their activity against HTRA1. Most of the peptides showed good inhibition, with Ahp25, Ahp26, Ahp27 and Ahp33 even having sub-μM $K_i$ values. This demonstrates that polar or nonpolar large side chains, especially with aromatic rings, can be present at position P2'. Likewise, also position P3 tolerates large amino acids such as halogen-substituted phenylalanine.

Example 4: Biological Determination of the Protease Activity hBMSC Culture and Osteogenic Differentiation Human BMSCs (hBMSCs) (Lonza Verviers, Belgium) were maintained in normal growth medium consisting of Dulbecco's modified eagle medium (DMEM-low glucose, with Glutamax) (Thermo Fisher Scientific, Reinach, Switzerland), supplemented with 10% fetal bovine serum (FBS) (Bioswisstec, Schaffhausen, Switzerland) and penicillin (50 units mL$^{-1}$) and streptomycin (50 μg mL$^{-1}$), and used between passage 2 and 6. The osteogenic differentiation of hBMSCs was performed as previously described in the art. Briefly, hBMSCs were seeded at 10'000 cells cm-2 in 24-well cell culture plates, and incubated for up to 14 days in osteogenic medium consisting of normal growth medium supplemented with ascorbic acid (50 μM), β-glycerophosphate (10 mM) and dexamethasone (100 nM) (all from Sigma-Aldrich, Buchs, Switzerland). Cells were replenished with fresh medium every 3-4 days. At 7 days post-osteogenic induction, cells were treated with 5 μg mL$^{-1}$ of catalytically active (HTRA1) or inactive (HTRA1SA) HTRA1 in the presence or absence of Ahp10 (27, 10 μM), and allowed to differentiate for a further 7 days. Mineralized matrix deposition by hBMSC-derived bone forming cells was visualized using Alizarin Red S, and the amount of staining quantified by determining the absorption at 570 nm using a multiplate reader (Infinite M200, Tecan) following extraction with 10% cetylpyridinium chloride (Sigma-Aldrich).

Results

As no defined cell culture-based assay for monitoring HTRA2 activity is yet available, we tested the bioactivity of Ahp-cyclodepsipeptides by monitoring osteogenesis of human bone marrow-derived stromal cells (hBMSCs), a process strictly dependent on HTRA1-mediated proteolysis. hBMSC-mediated matrix mineralization was visualized via Alizarin Red S staining after treatment with either 10 μM Ahp10 in the presence or absence of HTRA1 or the catalytically inactive mutant HTRA1 S328A (FIG. 2). These data demonstrated that Ahp10 significantly inhibited HTRA1-mediated hBMSC osteogenesis and thus the inhibition of HTRA1 by Ahp-cyclodepsipeptides in cell culture.

The invention claimed is:

1. An Ahp-cyclodepsipeptide having the following formula

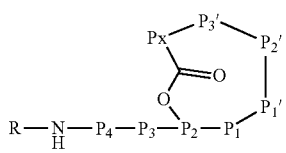

wherein
P1 is an α-amino acid with a cyclopropyl group as side chain;
P2 is an amino acid with a hydroxyl group in the side chain;
P3 is any amino acid;
P4 is any amino acid;
P1' is 5-hydroxy-norvaline forming a 3-amino-6-hydroxy-2-piperidone unit with the α-amino group of P2';
P2' is any amino acid;
P3' is an amino acid with a hydrophobic side chain comprising a methyl group attached to the α-amino group;
Px is any amino acid coupled with its α-carboxylic acid group to the hydroxyl group of P2, forming an ester bond;
R is hydrogen or a chemical group.

2. The Ahp-cyclodepsipeptide according to claim 1 which is capable of binding to a HTRA protease and reducing or inhibiting its protease activity.

3. The Ahp-cyclodepsipeptide according to claim 1, wherein
P1 is an α-amino acid with a cyclopropyl group as side chain;
P2 is threonine or (3-OH)-leucine;
P3 is alanine, valine, phenylalanine or phenylalanine wherein the phenyl group is substituted with halogen or a cyano group
P4 is alanine or valine
P1' is 5-hydroxy-norvaline forming a 3-amino-6-hydroxy-2-piperidone unit with the α-amino group of P2';
P2' is leucine, phenylalanine, phenylalanine wherein the phenyl group is substituted with halogen or a cyano group, glutamic acid, asparagine or an α-amino acid with a —CH$_2$CH$_2$CH$_2$NHC(=O)NH$_2$ group as side chain;
P3' is phenylalanine or tyrosine, in particular phenylalanine, comprising a methyl group attached to the a-amino group;
Px is alanine or valine coupled with its a-carboxylic acid group to the hydroxyl group of P2, forming an ester bond;
R is hydrogen or a C1-8 aliphatic or aromatic alkyl group forming an amide bond or a carbamate bond with the amino group to which it is attached.

4. The Ahp-cyclodepsipeptide according to claim 3, wherein
P2 is threonine.

5. The Ahp-cyclodepsipeptide according to claim 3, wherein
P3 is alanine, p-chlorophenylalanine, m-chlorophenylalanine, m-fluorophenylalanine or
m-cyanophenylalanine.

6. The Ahp-cyclodepsipeptide according to claim 3, wherein
P4 is alanine.

7. The Ahp-cyclodepsipeptide according to claim 3, wherein
P2' is leucine, phenylalanine, p-chlorophenylalanine, p-bromophenylalanine, m-fluorophenylalanine, m-cyanophenylalanine or an α-amino acid with a —CH$_2$CH$_2$CH$_2$NHC(=O)NH$_2$ group as side chain.

8. The Ahp-cyclodepsipeptide according to claim 3, wherein
P3' is phenylalanine.

9. The Ahp-cyclodepsipeptide according to claim 3, wherein
Px is valine.

* * * * *